United States Patent
Ray et al.

[19]

[11] Patent Number: 6,113,639
[45] Date of Patent: Sep. 5, 2000

[54] TRIAL IMPLANT AND TRIAL IMPLANT KIT FOR EVALUATING AN INTRADISCAL SPACE

[75] Inventors: Charles D. Ray, Williamsburg, Va.; Robert L. Assell, Mendota Heights, Minn.

[73] Assignee: Raymedica, Inc., Bloomington, Minn.

[21] Appl. No.: 09/274,535

[22] Filed: Mar. 23, 1999

[51] Int. Cl.[7] .................................................. A61F 2/44
[52] U.S. Cl. ........................................................ 623/17.16
[58] Field of Search ............................ 623/11, 17, 17.11, 623/17.16; 606/53, 60, 61; 33/511, 512

[56] References Cited

U.S. PATENT DOCUMENTS

| | | |
|---|---|---|
| 4,772,287 | 9/1988 | Ray et al. . |
| 4,904,260 | 2/1990 | Ray et al. . |
| 4,946,378 | 8/1990 | Hirayama et al. . |
| 5,123,926 | 6/1992 | Pisharodi . |
| 5,306,309 | 4/1994 | Wagner et al. ............................ 623/17 |
| 5,390,683 | 2/1995 | Pisharodi . |
| 5,443,514 | 8/1995 | Steffee . |
| 5,458,643 | 10/1995 | Oka et al. . |
| 5,505,732 | 4/1996 | Michelson . |
| 5,534,029 | 7/1996 | Shima ........................................ 623/17 |
| 5,674,295 | 10/1997 | Ray et al. .................................. 623/17 |
| 5,676,702 | 10/1997 | Ratron . |
| 5,716,415 | 2/1998 | Steffee . |
| 5,766,252 | 6/1998 | Henry et al. . |
| 5,888,224 | 3/1999 | Beckers et al. . |

FOREIGN PATENT DOCUMENTS

| | | |
|---|---|---|
| 39 22 203 C1 | 10/1990 | Germany . |
| 405208029 | 8/1993 | Japan ....................................... 623/17 |

OTHER PUBLICATIONS

J.N. Weinstein, 'The Artificial Disc', Clinical Efficacy and Outcome in the Diagnosis and Treatment of Low Back Pain, pp. 205–225, Published 1992.

*Primary Examiner*—John J. Wilson
*Assistant Examiner*—Eduardo C. Robert
*Attorney, Agent, or Firm*—Dicke, Billig & Czaja, P.A.

[57] ABSTRACT

A trial implant for evaluating a size of an intradiscal space for subsequent implantation of a prosthetic spinal disc nucleus. The trial implant is comprised of an elongated central body and a retrieving body. The elongated body is formed from a rigid, surgically safe material and preferably has a volume less than a volume of a nucleus cavity portion of the intradiscal space. The retrieving body is associated with the central body and is configured to facilitate retrieval of the trial implant from an enclosed area, such as the nucleus cavity. A plurality of trial implants are included with a trial implant kit, with each of the plurality of trial implants housing a different size and/or shape. During use, the trial implant provides an indication as to whether a similarly sized prosthetic spinal disc nucleus will fit within a particular intradiscal space.

40 Claims, 11 Drawing Sheets

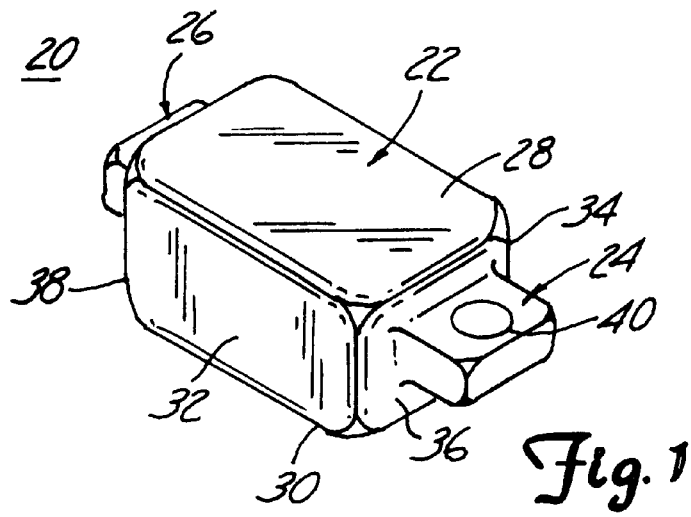
Fig. 1
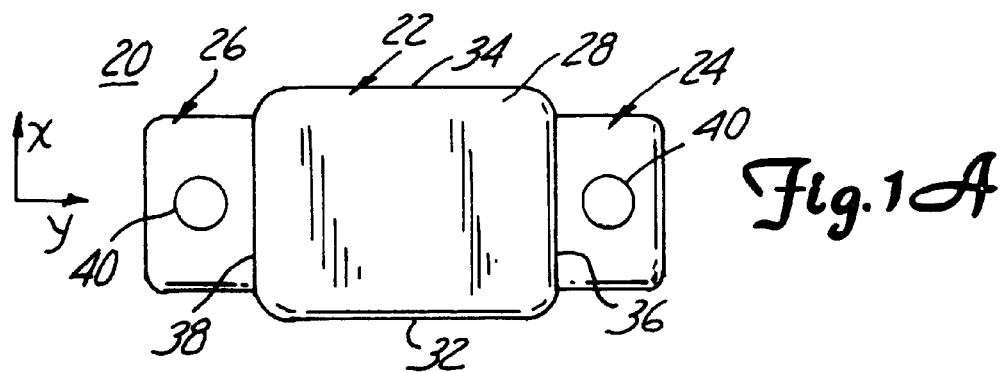
Fig. 1A
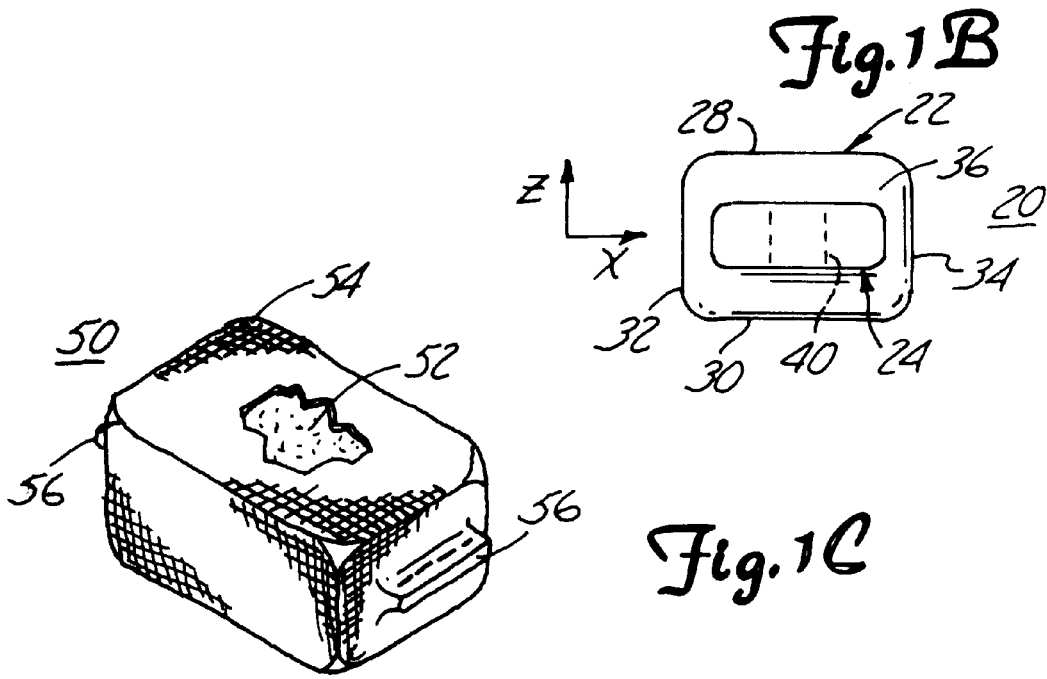
Fig. 1B
Fig. 1C

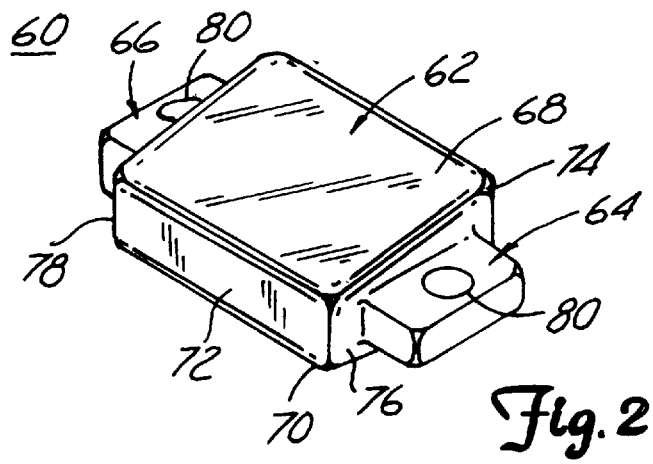
Fig. 2
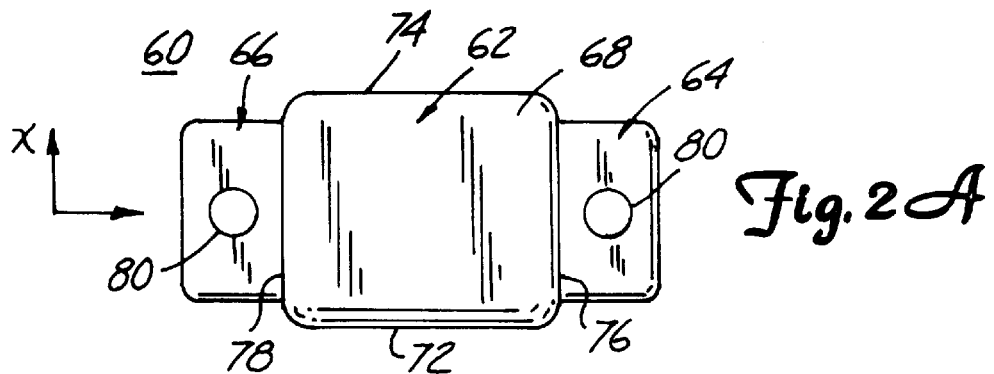
Fig. 2A
Fig. 2B
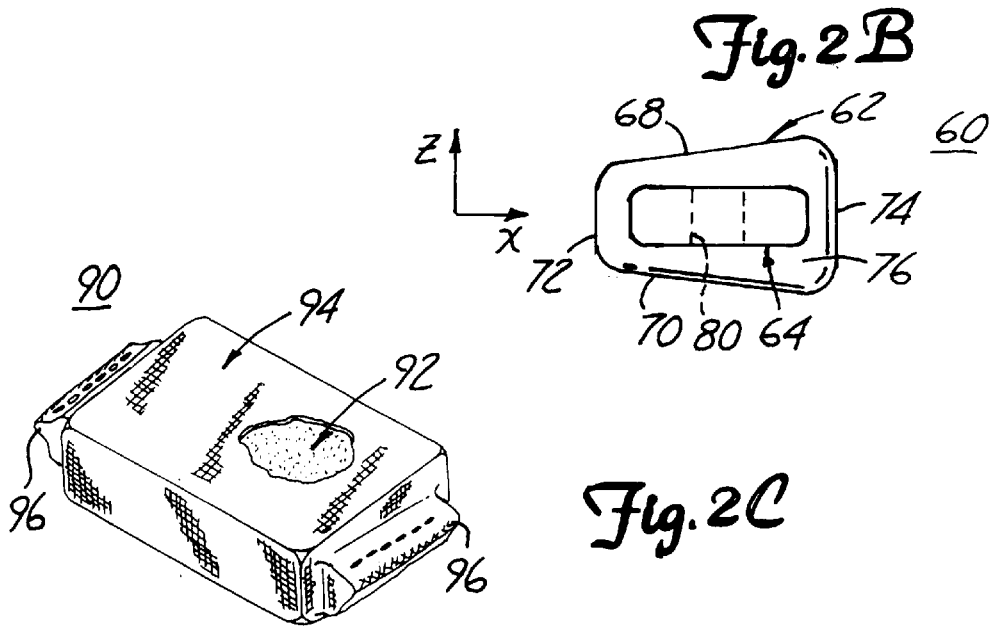
Fig. 2C

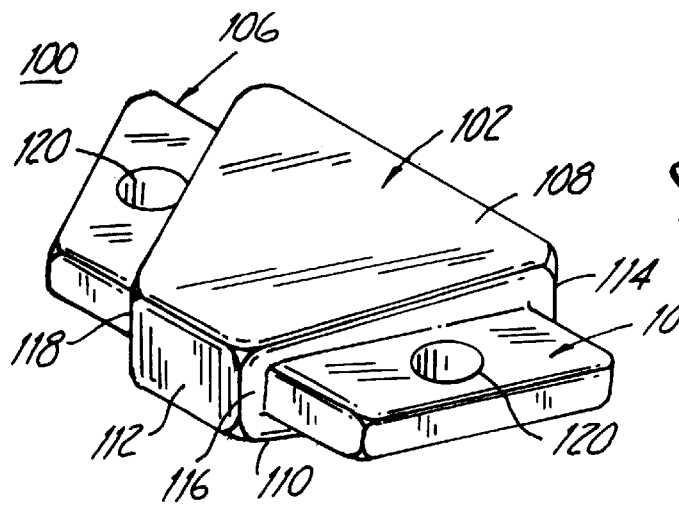
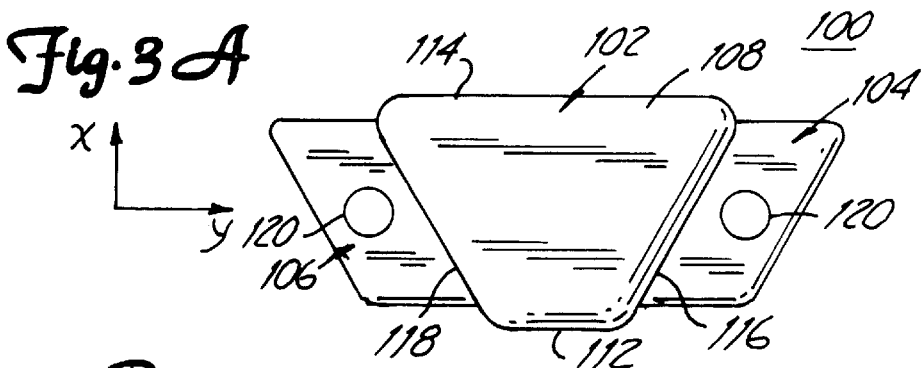
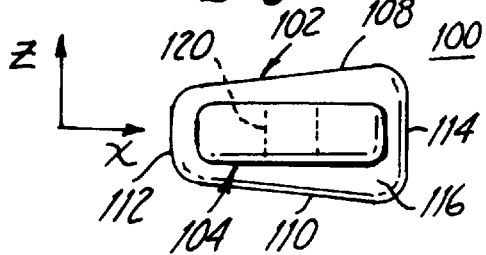
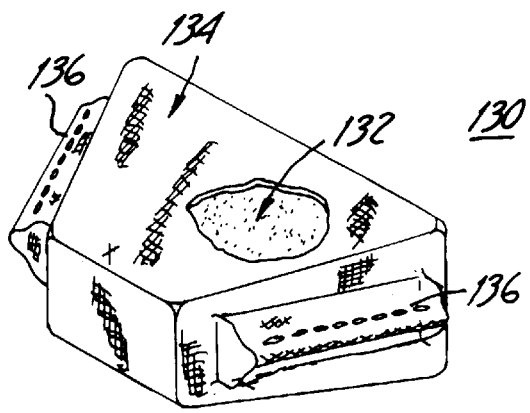

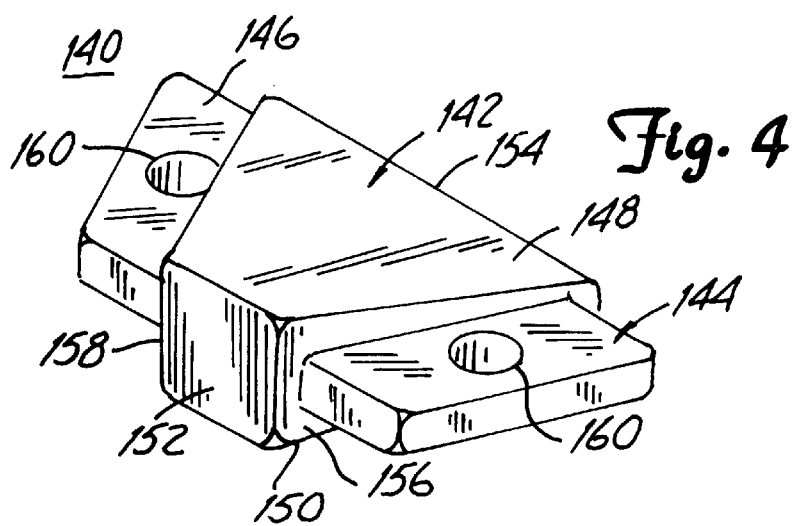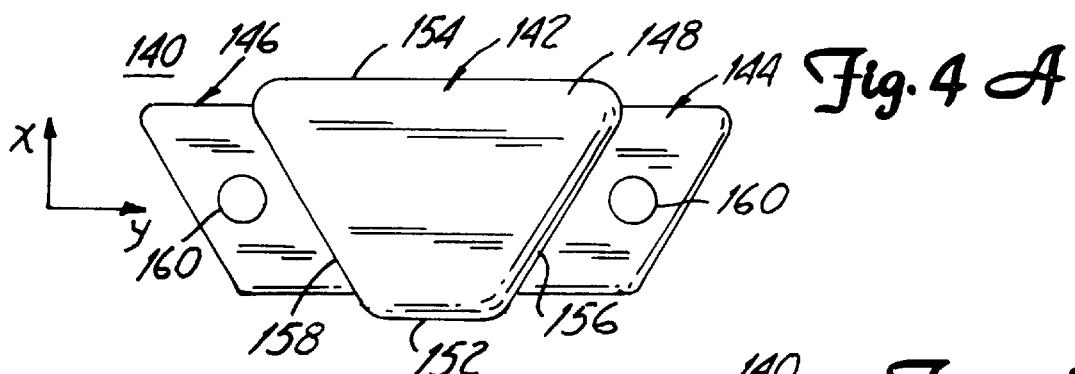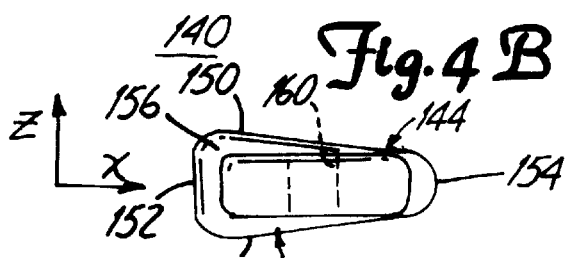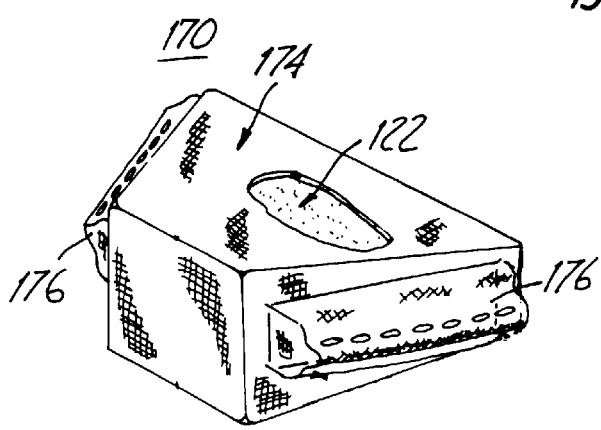

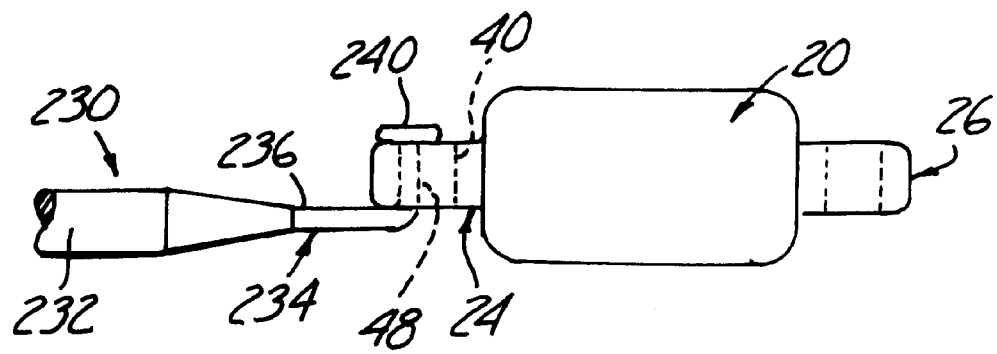
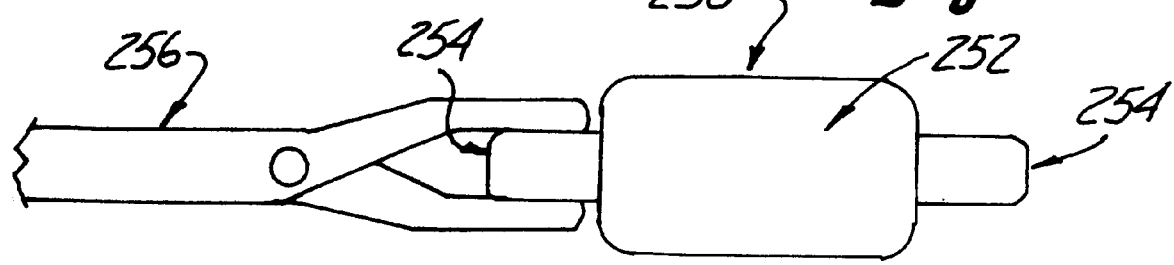

TRIAL IMPLANT AND TRIAL IMPLANT KIT FOR EVALUATING AN INTRADISCAL SPACE

BACKGROUND OF THE INVENTION

The present invention relates to an intradiscal trial implant device. More particularly, it relates to a trial implant and a trial implant kit for use in evaluating an intradiscal space, including an anulus and nucleus cavity, and for assisting a surgeon in the selection of an appropriately sized prosthetic spinal disc nucleus.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, with a neural (vertebral) arch that arises from a posterior surface of the vertebral body. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as a lamina. Projecting from the posterior region of the neural arch is a spinous process. The central portions of adjacent vertebrae are supported by the intervertebral disc.

The intervertebral disc primarily serves as a mechanical cushion between the vertebral bones, permitting controlled motions within vertebral segments of the axial skeleton. The normal disc is a unique, mixed structure, comprised of three component tissues. The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30-degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the opposing vertebral bodies. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into, and released from, the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates the normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal load cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space (as opposed to only the nucleus), and were large and rigid. Beyond the questionable efficacy of these devices was the inherent difficulties encountered during implantation. Due to their size and inflexibility, these devices required an anterior implantation approach as the barriers presented by the lamina and, more importantly, the spinal cord and nerve rootlets during posterior implantation could not be avoided. Recently, smaller and more flexible prosthetic nucleus devices have been developed. With the reduction in prosthesis size, the ability to work around the spinal cord and nerve rootlets with a posterior implantation is now possible.

For example, Ray et al., U.S. Pat. No. 5,647,295 discloses a hydrogel-based prosthetic nucleus that is implanted into the intradiscal space in a dehydrated state. The Ray et al. prosthesis includes a jacket sized to constrain expansion of the hydrogel core. More particularly, following implant, the constraining jacket directs the hydrogel to expand primarily in height, thereby separating adjacent vertebrae. The prosthetic spinal disc nucleus of Ray et al. is sized such that in a final hydrated form, the prosthesis has a volume much less than a volume of the nucleus cavity. In this way, two prostheses can be orientated in a side-by-side fashion within the nucleus cavity. With this dual-prosthesis approach, only a small incision in the anulus is required for implantation, thereby limiting damage to the anulus.

Variations to the Ray et al. prosthesis have been envisioned, including pre-shaping the hydrogel core to more closely correspond with the inherent shape of a portion of a particular nucleus cavity. More particularly, the hydrogel core may be pre-formed to assume a wedge shape to accommodate height variations at the anterior or posterior side of the intradiscal space.

While the device of Ray et al., along with the above-described variations and other similar products, are clearly beneficial, selection of a properly sized prosthesis may be difficult. In this regard, while the individual intradiscal spaces making up the human spine are, relatively speaking, similar, distinctions in terms of shape and size exist. For example, a central area of the L4-L5 intradiscal space has an increased height at a central portion in comparison with the posterior and anterior sides. Conversely, the L5-S1 intradiscal space typically has an essentially uniform increase in height from the posterior side to the anterior side. Even further, the shape and size characteristics of a particular disc space may vary greatly from person to person. Finally, unforeseen impediments within the intradiscal space itself may limit the area available to receive the prosthesis. For example, Ray et al. describes preferably removing the entire nucleus prior to implanting the prosthetic spinal disc nuclei. While every effort is made to accomplish this result, invariably some nucleus tissue remains within the nucleus cavity. This excess tissue may reduce the available area of the nucleus cavity, thereby limiting proper implantation of a certain sized prosthesis.

While the Ray et al. prostheses, and variations thereof, do not rely upon the anulus for constraining the hydrogel core, certain dimensional concerns remain. It is generally desirable that each of the two implanted prostheses corresponds as closely as possible to the region of the intradiscal space receiving the implant. For example, with Ray et al., a first one of the two prostheses may be implanted at the anterior side of the intradiscal space, extending transversely within the nucleus cavity. As a point of reference, the second prosthesis is implanted at the posterior side of the intradiscal space, again extending in a transverse fashion. With this orientation, the first prosthesis must be sized to have a length approximating a transverse diameter of the nucleus cavity at the anterior side thereof. Additionally, the prosthesis must be sized to satisfy the above-described height variations of a nucleus cavity.

In light of the above, it may be difficult for a surgeon to accurately select an appropriately sized prosthetic spinal disc nucleus. Due to the enclosed nature of the nucleus cavity, it is virtually impossible for the surgeon to accurately evaluate the size and shape of a particular nucleus cavity. In this regard, X-rays reveal little, if any, of the details of a discal region. As a result, the surgeon is normally forced to estimate the nucleus cavity based upon the patient's height, weight, the particular intradiscal space in question, etc. While this method of estimation is normally sufficient, occasionally an incorrectly sized prosthesis is selected, leading to possible problems. If, for example, too large a prosthesis is chosen, the surgeon will be unable to optimally position the device within the nucleus cavity. In fact, the surgeon may find it impossible to insert the prosthesis into the disc space or to achieve proper orientation. Conversely, where the selected prosthesis is too small, sufficient support may not be provided, potentially resulting in disc failure. Unfortunately, in either case, the surgeon will not be aware of the sizing problem until after he or she has attempted to implant the prosthetic spinal disc nucleus. As a result, the prosthetic spinal disc nucleus will have been in direct contact with blood and other bodily fluids. Where the prosthetic spinal disc nucleus includes a woven outer jacket, or a cover composed of a similar material, it is virtually impossible to resterilize the prosthesis. Thus, the prosthetic spinal disc nucleus, normally an expensive device, must be discarded.

The prosthetic spinal disc nucleus has been shown to be a highly useful tool for correcting degenerated intervertebral discs. However, the inability to accurately evaluate a disc space prior to implant may lead to complications. Therefore, a need exists for a device or kit used to evaluate an available internal area of an intradiscal space and assist in selecting a properly sized prosthetic spinal disc nucleus.

SUMMARY OF THE INVENTION

The present invention provides a trial implant for evaluating a size of a nucleus cavity for subsequent implantation of a prosthetic spinal disc nucleus. In a preferred embodiment, the trial implant is comprised of an elongated central body and a retrieving means. The retrieving means is associated with the elongated central body and in one preferred embodiment is an integrally formed tab.

The elongated central body is formed from a rigid, surgically safe material and has a volume less than a volume of the nucleus cavity. Further, the elongated central body defines a superior face, an inferior face, opposing side faces and opposing end faces. In one preferred embodiment, each of the various faces of the elongated central body is relatively smooth, and corresponds with a size and shape of an available prosthetic spinal disc nucleus.

The retrieving means is configured to facilitate retrieval of the trial implant from an enclosed area, such as the nucleus cavity. For example, in one preferred embodiment, the retrieving means is a tab extending from one of the opposing end faces, sized to be grasped by a hemostat. Taken in combination, in one preferred embodiment, the elongated central body and the retrieving means are sized in accordance with an available prosthetic spinal disc nucleus.

Another aspect of the present invention relates to a trial implant for evaluating a size of a nucleus cavity portion of an intradiscal space. The trial implant is comprised of an elongated body having a volume that is less than a volume of the nucleus cavity. The elongated body is formed of a rigid, non-porous material. The rigid, non-porous material facilitates repeated use of the trial implant in that it does not absorb blood or other bodily fluids and can be repeatedly sterilized.

Another aspect of the present invention relates to a kit for use in evaluating a size of a nucleus cavity prior to implanting a prosthetic spinal disc nucleus. The nucleus cavity is defined by an opposing pair of vertebral bodies and an anulus. The kit includes a container, a first trial implant body and a second trial implant body. The first trial implant body and the second trial implant body are selectively maintained within the container.

The container maintains the first trial implant body and the second trial implant body such that the trial implant bodies are accessible by a user. In one preferred embodiment, the container is made of material able to withstand repeated heat sterilization, such as in an autoclave.

The first trial implant body is formed of a rigid, surgically safe material and has a predetermined size and shape. In one preferred embodiment, the first trial implant body has a volume less than a volume of the nucleus cavity.

The second trial implant body is formed of a rigid, surgically safe material and has a predetermined size and shape. The predetermined size of the second trial implant body is different from the size of the first trial implant body.

During use, a user prepares a discal area by creating an access site to the nucleus cavity. The first trial implant body is retrieved from the container. The user then attempts to insert the first trial implant body into the nucleus cavity. An evaluation of a size of the access site and the nucleus cavity is made based upon the attempted insertion. The first trial implant body is then returned to the container. In a preferred embodiment, the user attempts to insert the second trial implant body into the nucleus cavity, again evaluating the access site and the nucleus cavity based upon the results of the attempted insertion. Following use, the container, including the first trial implant body and the second trial implant body, are sterilized for subsequent reuse.

Another aspect of the present invention relates to a method of evaluating a size of a nucleus cavity for receiving a prosthetic spinal disc nucleus. In this regard, the nucleus cavity is defined by an opposing pair of vertebral bodies and an anulus. The method includes creating an opening in the anulus to provide access to the nucleus cavity. A trial implant body is then inserted into the nucleus cavity through the opening. The trial implant body is made of a rigid, surgically safe material and has a known size and shape. As part of the insertion process, an attempt is made to position the trial implant body within a desired portion of the nucleus cavity. A determination is made as to whether the trial implant body fits within the desired portion of the nucleus cavity. Finally, the trial implant body is removed from the nucleus cavity.

BRIEF DESCRIPTION OF THE DRAWINGS

FIG. 1 is a perspective view of a trial implant in accordance with the present invention;

FIG. 1A is a top view of the trial implant of FIG. 1;

FIG. 1B is a side view of the trial implant of FIG. 1;

FIG. 1C is a perspective view of an available prosthetic spinal disc nucleus to which the trial implant of FIG. 1 corresponds;

FIG. 2 is a perspective view of an alternative embodiment of a trial implant in accordance with the present invention;

FIG. 2A is top view of the trial implant of FIG. 2;

FIG. 2B is a side view of the trial implant of FIG. 2;

FIG. 2C is a perspective view of an available prosthetic spinal disc nucleus to which the trial implant of FIG. 2 corresponds;

FIG. 3 is a perspective view of an alternative embodiment of a trial implant in accordance with the present invention;

FIG. 3A is a top view of the trial implant of FIG. 3;

FIG. 3B is a side view of the trial implant of FIG. 3;

FIG. 3C is a perspective view of an available prosthetic spinal disc nucleus to which the trial implant of FIG. 3 corresponds;

FIG. 4 is perspective view of an alternative embodiment of a trial implant in accordance with the present invention;

FIG. 4A is a top view of the trial implant of FIG. 4;

FIG. 4B is a side view of the trial implant of FIG. 4;

FIG. 4C is a perspective view of an available prosthetic spinal disc nucleus to which the trial implant of FIG. 4 corresponds;

FIGS. 11–13 illustrate various techniques for removing a trial implant from a nucleus cavity;

DETAILED DESCRIPTION OF THE PREFERRED EMBODIMENTS

A. Trial Implant 20

Figure 5:
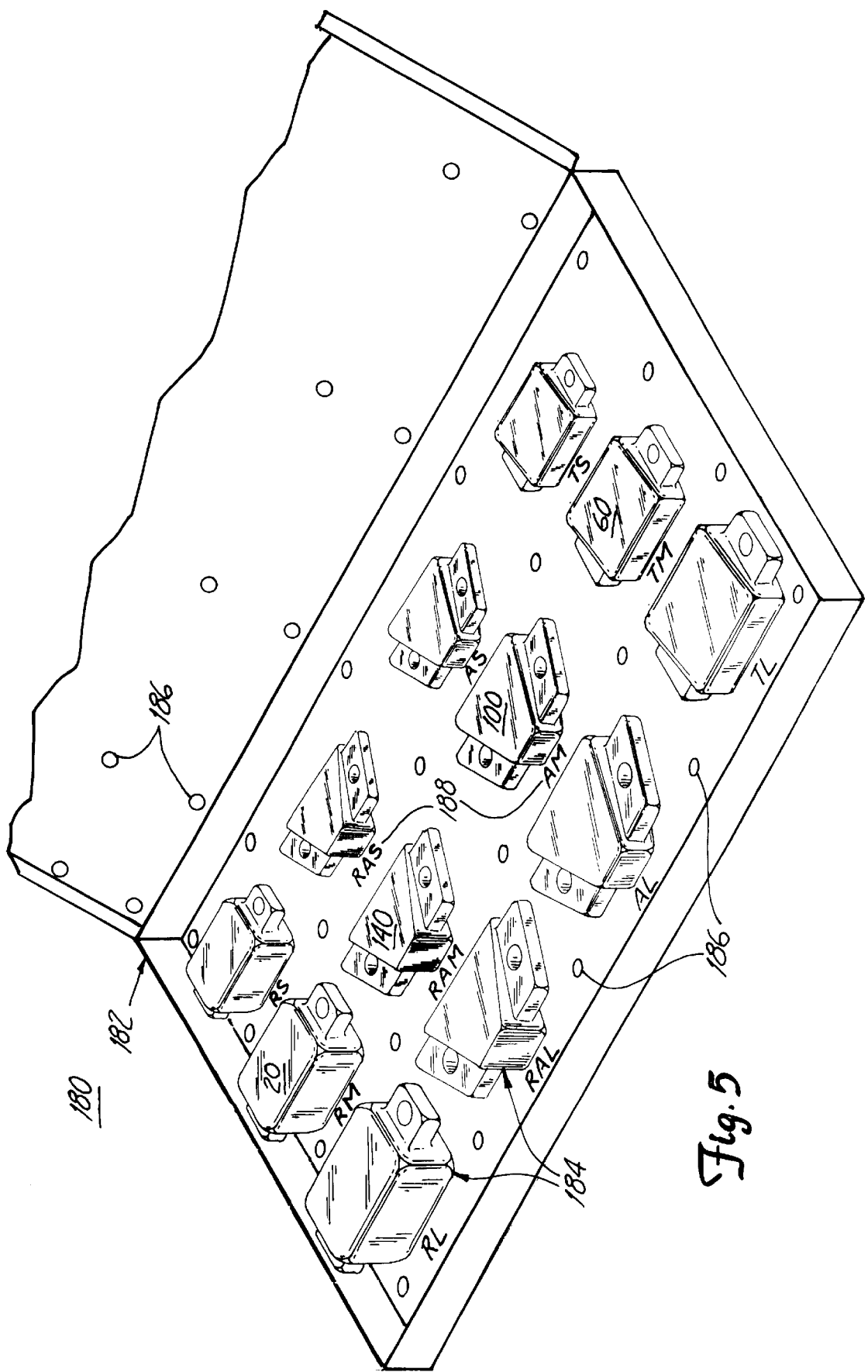
FIG. 5 is an elevated view of a kit for evaluating a size of a nucleus cavity.
Figure 6:
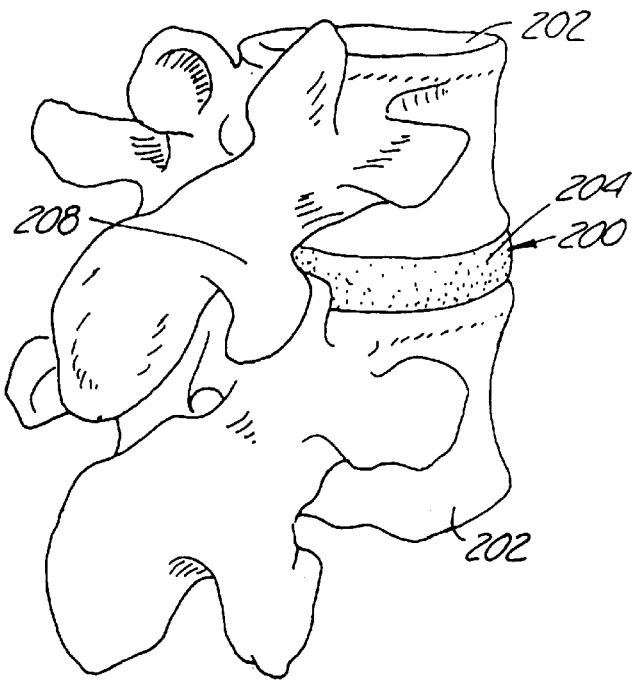
FIG. 6 is an elevated view of a spinal segment including a degenerated discal area.

One preferred embodiment of a trial implant 20 is shown in FIG. 1. The trial implant 20 is comprised of an elongated central body 22, a first tab 24 and a second tab 26. The first tab 24 and the second tab 26 extend from opposite sides of the central body 22.

The central body 22 defines a superior face 28, an inferior face 30, an anterior side face 32, a posterior side face 34, a first end face 36 and a second end face 38. For the purposes of this disclosure, directional terminology such as "superior," "inferior," "anterior," and "posterior" are with reference to one possible orientation of the trial implant 20 within a nucleus cavity (not shown). It should be understood, however, that due to its unique sizing, the trial implant 20 can be orientated in any direction relative to a nucleus cavity or the world in general. As such, the directional terms are provided for purposes of illustration only, and should not be interpreted as limitations.

As shown more clearly in FIGS. 1A and 1B, the central body 22 is fabricated to assume an elongated rectangular shape. In this regard, a top view (FIG. 1A) of the trial implant 20 depicts the superior face 28 as being substantially rectangular. In one preferred embodiment, the inferior face 30 (FIG. 1) is virtually identical to the superior face 28.

Additionally, a side view (FIG. 1B) depicts the second end face 38 of the central body 22 as being substantially rectangular. In one preferred embodiment, the first end face 36 is virtually identical to the second end face 38.

The central body 22 is preferably made of a rigid, surgically safe (or passive, inert) material, able to maintain its structural integrity upon repeated sterilization. As described below, the central body 22 will preferably be subjected to repeated sterilization in an autoclave, such that the material used for the central body 22 is "autoclavable." Further, the material is preferably non-porous such that it will not readily absorb blood or other fluids. For example, in one preferred embodiment, the central body 22 is formed from polyvinylideneflouride, such as Kynar®, available from DuPont, Inc. Alternatively, other rigid, autoclave-sterilizable materials, such as stainless steel, aluminum, teflon, ceramics, etc. are also available. In the preferred embodiment, however, the material selected for the elongated body is sufficiently tough (or has a sufficient modulus of toughness) for repeated use. For example, polyvinylideneflouride and similar materials are sufficiently tough so that the central body 22 will not break when grasped by a tool, yet maintain its structural integrity when being forced into a particular location. Conversely, for example, materials such as acrylics, ceramics and polycarbonate are likely too brittle, whereas materials such as silicone rubber, polyurethane rubber and teflon are likely too malleable. Finally, the material selected for the central body 22 preferably has a low friction attribute. In this regard, to facilitate insertion of the trial implant 20 into an enclosed area, such as a nucleus cavity, the control body 22 is preferably configured such that the superior face 28, the anterior face 30, the side faces 32, 34 and faces 36, 38 are relatively smooth.

The first tab 24 and the second tab 26 are virtually identical, each including an opening 40. The first tab 24 and the second tab 26 extend from opposite sides of the elongated central body 22. For example, the first tab 24 extends from the first end face 36; whereas the second tab 26 extends from the second end face 38. As described in greater detail below, the first tab 24 and the second tab 26 are configured to facilitate retrieval of the trial implant 20 from an enclosed area, such as a nucleus cavity, and therefore are appropriately referred to as retrieving means.

In a preferred embodiment, the first and second tabs 24, 26 are integrally formed with the elongated central body 22. Alternatively, the first and second tabs 24, 26 may be formed as separate components, subsequently attached to the elongated central body 22. Regardless of exact construction, the first and second tabs 24, 26 are preferably made of the same material as the elongated central body 22. Thus, the first and second tabs 24, 26 are made of a rigid, surgically safe material able to maintain its structural integrity when subjected to repeated sterilization (such as with an autoclave). For example, the first and second tabs 24, 26 are composed of polyvinylideneflouride, although other rigid materials are also acceptable. Further, in a preferred embodiment, the material selected for the tabs 24, 26 is non-porous and tough. Additionally, in one preferred embodiment, the first and second tabs 24, 26 are configured to reflect shape characteristics of an available prosthetic spinal disc nucleus, as described in greater detail below.

One method of using the trial implant 20 is provided in greater detail below.

Generally speaking, however, the trial implant 20 is sized and shaped to simulate the size and shape of an available prosthetic spinal disc nucleus. An example of one such prosthetic spinal disc nucleus 50 is shown in FIG. 1C. The prosthetic spinal disc nucleus 50 is generally comprised of a hydrogel core 52 and a constraining jacket 54. The constraining jacket 54 typically made of a woven material and is secured about the hydrogel core 52 by closures 56 located at opposite sides of the hydrogel core 52. The hydrogel core 52 is pre-formed to assume a rectangular shape, and is configured to expand from a dehydrated state to a hydrated state. The constraining jacket 54 constrains expansion of the hydrogel core 52 in the hydrated state. The prosthetic spinal disc nucleus 50 is typically implanted in the dehydrated state, and can be manufactured to various dimensions while still adhering to the depicted generally rectangular shape. Due to the woven nature of the constraining jacket 54, it is difficult, if not impossible, to "resterilize" the prosthetic spinal disc nucleus 50 once exposed to blood or other bodily fluids.

Comparison of the trial implant 20 of FIG. 1 with the prosthetic spinal disc nucleus 50 of FIG. 1C illustrates the general correspondence in size and shape of the trial implant 20 with the prosthetic spinal disc nucleus 50. Because the trial implant 20 is representative of the prosthetic spinal disc nucleus 50 (preferably in a dehydrated state) in terms of shape and size, the trial implant 20 can be used to evaluate whether the prosthetic spinal disc nucleus 50 is of an appropriate size for a particular disc space. In this regard, it should be noted that the first and second tabs 24, 26 are representative of the closures 56. It should be understood that the prosthetic spinal disc nucleus 50 shown in FIG. 1C is but one example of an available prosthesis. Other prosthetic nucleus devices are available that vary in size and construction from the one depicted in FIG. 1C. For example, the trial implant 20 may correspond with a prosthetic nucleus utilizing a material other than the hydrogel core 52 and/or the constraining jacket 54 of the prosthetic spinal disc nucleus 50 shown in FIG. 1C. In fact, the particular prosthesis may not include the closures 56. With this prosthesis configuration, the first and second tabs 24, 26 may be eliminated from the trial implant 20.

Given the above design considerations, the trial implant 20 may assume a variety of sizes, yet satisfy the preferred rectangular shape. In one preferred embodiment, the trial implant 20 has an overall length (y-axis in FIG. 1A) in the range of approximately 0.5–1.5 inches ($\approx$12.5–38.0 mm). In this regard, the elongated central body 22 has a length in the range of approximately 0.3–0.9 inch ($\approx$7.5–23.0 mm), whereas each of the first and second tabs 24, 26 has a length in the range of approximately 0.1–0.3 inch ($\approx$2.5–7.5 mm). Further, the central body 22 has a height (z-axis in FIG. 1B) in the range of approximately 0.1–0.5 inch ($\approx$2.5–12.5 mm) and a width (x-axis in FIGS. 1A and 1B) in the range of approximately 0.2–0.6 inch ($\approx$5–15 mm). The first and second tabs 24, 26 each have a height (z-axis in FIG. 1B) in the range of approximately 0.02–0.22 inch ($\approx$0.5–5.5 mm) and a width (x-axis in FIGS. 1A and 1B) slightly less than that of the central body 22. Finally, the hole 40 in each of the first and second tabs 24, 26 has a diameter in the range of approximately 0.05–0.15 inch ($\approx$1–4 mm).

It is understood that individual disc spaces vary in terms of shape and size. To accommodate these variations, the trial implant 20 is preferably made available in a variety of sizes. As described in greater detail below, the most important concerns relate to the length (y-axis in FIG. 1A) and the height (z-axis in FIG. 1B) of the trial implant 20, and in particular the central body 22. Within the above dimensional parameters, at least six versions of the trial implant 20 are preferably available, having the central body 2 is sized in accordance with the following table:

|   | Central Body 22<br>Height (z-axis) | Central Body 22<br>Length (y-axis) |
|---|---|---|
| 1 | 0.23 inch (5.8 mm) | 0.45 inch (11.5 mm) |
| 2 | 0.23 inch 5.8 mm) | 0.74 inch (18.8 mm) |
| 3 | 0.31 inch (7.9 mm) | 0.45 inch (11.5 mm) |
| 4 | 0.31 inch (7.9 mm) | 0.74 inch (18.8 mm) |
| 5 | 0.38 inch (9.7 mm) | 0.45 inch (11.5 mm) |
| 6 | 0.38 inch (9.7 mm) | 0.74 inch (18.8 mm) |

Generally speaking, regardless of the exact size of the central body 22, the first and second tabs 24, 26 have approximately the same dimensional characteristics. In this regard, each of the first and second tabs 24, 26 has a height (z-axis) of approximately 0.12 inch (≈3.0 mm) and a length (y-axis) of approximately 0.20 inch (≈5 mm).

B. Trial Implant 60

As previously described, the trial implant 20 is preferably shaped to imitate the shape of an available prosthetic spinal disc nucleus. One example of the prosthetic spinal disc nucleus 50 was shown in FIG. 1C as being generally rectangular. A variety of differently shaped prosthetic disc nuclei are also available. As a result, the trial implant 20 can be modified to simulate these other shapes. One example of an alternative embodiment, trial implant 60 is shown in FIG. 2. Similar to the trial implant 20 (FIG. 1), the alternative embodiment trial implant 60 is preferably comprised of an elongated central body 62, a first tab 64 and a second tab 66. The first tab 64 and the second tab 66 extend from opposite sides of the central body 62.

The central body 62 defines a superior face 68, an inferior face 70, an anterior side face 72, a posterior side face 74, a first end face 76 and a second end face 78. As shown more clearly in FIGS. 2A and 2B, the central body 62 is fabricated to assume a tapered, rectangular shape. For purposes of identification, then, the trial implant 60 can be referred to as a "tapered trial implant," whereas the trial implant 20 (FIG. 1) can be referred to as a "rectangular trial implant." With respect to the tapered trial implant 60, a top view (FIG. 2A) shows the superior face 68 as being substantially rectangular. In one preferred embodiment, the inferior face 70 is virtually identical to the superior face 68. Additionally, a side view (FIG. 1B) depicts the second end face 78 as tapered or wedge shaped. The first end face 76 is preferably virtually identical to the second end face 78.

With reference to FIG. 2A, the top view of the tapered trial implant 60 defines a width (x-axis in FIG. 2A) and length (y-axis in FIG. 2A). Further, the side view of the tapered trial implant 60 defines the width (x-axis in FIG. 2B) and a height (z-axis in FIG. 2B). As shown in FIG. 2B, the central body 62 has a height (z-axis) increasing from the posterior side face 74 to the anterior side face 72. With reference to FIG. 2B, the central body 62 is formed such that each of the superior face 68 and the inferior face 70 form an angle relative to the posterior side face 74 in the range of approximately 92–100 degrees such that the central body 62 has an included angle in the range of 4–20 degrees, preferably 12 degrees.

The central body 62 is virtually identical to the central body 22 (FIG. 1) previously described in terms of construction. Thus, the central body 62 is preferably made of a rigid, surgically safe material able to maintain its structural integrity when subjected to repeated sterilization, such as with an autoclave Further, the various faces 68–78 are all relatively smooth to facilitate insertion of the tapered trial implant 60 into a nucleus cavity (not shown).

The first tab 64 and the second tab 66 are virtually identical, each including an opening 80. The first tab 64 and the second tab 66 extend from opposite sides of the central body 62. For example, the first tab 64 extends from the first end face 76; whereas the second tab 66 extends from the second end face 78. As described in greater detail below, the first tab 64 and the second tab 66 are configured to facilitate retrieval of the trial implant 60 from an enclosed area, such as a nucleus cavity, and therefore are correctly referred to as retrieving means. Similar to the central body 62, the first and second tabs 64, 66 are preferably made of a rigid, surgically safe material able to maintain structural integrity when subjected to repeated sterilization (such as with an autoclave). Additionally, the first and second tabs 64, 66 are configured to reflect sizing characteristics of an available prosthetic spinal disc nucleus, as described in greater detail below.

Similar to the rectangular trial implant 20 (FIG. 1) previously described, the tapered trial implant 60 is sized and shaped to generally correspond with the size and shape of an available prosthetic spinal disc nucleus. An example of one such tapered prosthetic spinal disc nucleus 90 is shown in FIG. 2C. The tapered prosthetic spinal disc nucleus 90 is generally comprised of a hydrogel core 92 and a constraining jacket 94. The constraining jacket 94 is secured about the hydrogel core 92 by closures 96 located at opposite ends of the hydrogel core 92. The hydrogel core 92 is pre-formed to assume a tapered shape, and is configured to expand from a dehydrated state to a hydrated state. The constraining jacket 94 constrains expansion of the hydrogel core 92 in the hydrated state. The tapered prosthetic spinal disc nucleus 90 is typically implanted in the dehydrated state, and can be manufactured to various dimensions while still maintaining the depicted tapered shape.

Comparison of the tapered trial implant 60 of FIG. 2 with the tapered prosthetic spinal disc nucleus 90 of FIG. 2C illustrates the general correspondence in size and shape of the tapered trial implant 60 with the tapered prosthetic spinal disc nucleus 90 (preferably in the dehydrated state). In a preferred embodiment, the first and second tabs 64, 66 correspond with the closures 96 of the tapered prosthetic spinal disc nucleus 90. It should be understood that the tapered prosthetic spinal disc nucleus 90 shown in FIG. 2C is but one example of an available prosthesis. Other prosthetic nucleus devices are available that vary in size and construction from the one depicted in FIG. 2C. The tapered trial implant 60 may be configured to correlate with the specific size and shape characteristics of these varying prostheses. In this regard, the first and second tabs 64, 66 may be eliminated.

With the above design characteristics of the tapered trial implant 60 in mind, in one preferred embodiment the tapered trial implant 60 has an overall length in the range of 0.5–1.6 inch (≈12.5–40.5 mm). The central body 62 has a length (y-axis in FIG. 2A) in the range of approximately 0.3–1.0 inch (≈7.5–25.5 mm)and a width (x-axis in FIG. 2A) in the range of approximately 0.3–0.7 inch (≈7.5–18 mm). As shown in FIG. 2B, the height (z-axis) of the central body 62 tapers from a maximum height at the anterior side face 72 to a minimum height at the posterior side face 74. With this construction in mind, in a preferred embodiment, the central body 62 has a maximum height (or anterior side face 72 height) in the range of approximately 0.1–0.5 inch (2.5–12.5 mm)and a minimum height (or posterior side face 74 height) in the range of approximately 0.05–0.4 inch (≈1–10 mm). The first and second tabs 64, 66 are virtually identical, having a length (y-axis in FIG. 2A) in the range of approximately 0.1–0.3 inch (≈2.5–7.5 mm) and a height (z-axis in FIG. 2B) in the range of approximately 0.1–0.2 inch (≈2.5–5 mm). It should be recognized that the above-provided dimensions can vary widely such that the tapered trial implant 60 is sized to evaluate any individual disc space.

Once again, the tapered trial implant 60 is preferably configured to match the size and of an available prosthetic spinal disc nucleus, such as the tapered prosthetic spinal disc us 90 shown in FIG. 2C. Due to the variations in size of individual disc spaces, the ed prosthetic spinal disc nucleus 90 is made available to a surgeon in different sizes. As a result, the tapered trial implant 60 should also be fabricated in a number of different sizes. In one preferred embodiment, at least six different sizes of the tapered trial implant 60, and in particular the central body 62, are available. In this regard, the central body 62 has a width is in FIG. 2B) of approximately 0.5 inch (≈13 mm), in conjunction with varying length height dimensions in accordance with the following table:

|   | Central Body 62 Maximum Height (z-axis) | Central Body 62 Minimum Height (z-axis) | Central Body 62 Length (y-axis) |
|---|---|---|---|
| 1 | 0.22 inch (5.6 mm) | 0.12 inch (3.0 mm) | 0.55 inch (14.0 mm) |
| 2 | 0.22 inch (5.6 mm) | 0.12 inch (3.0 mm) | 0.74 inch (18.8 mm) |
| 3 | 0.29 inch (7.4 mm) | 0.19 inch (4.8 mm) | 0.55 inch (14.0 mm) |
| 4 | 0.29 inch (7.4 mm) | 0.19 inch (4.8 mm) | 0.74 inch (18.8 mm) |
| 5 | 0.37 inch (9.4 mm) | 0.27 inch (6.9 mm) | 0.55 inch (14.0 mm) |
| 6 | 0.37 inch (9.4 mm) | 0.27 inch (6.9 mm) | 0.74 inch (18.8 mm) |

Regardless of the exact size of the central body 62, the first and second tabs 64, 66 are virtually identical, having a length (y-axis) of approximately 0.20 inch (≈5 mm) and a axis) of approximately 0.12 inch (≈3.0 mm). Finally, the opening 80 associated the first tab 64 and the second tab 66 has a diameter of approximately 0.10 inch (≈2.5 mm).

C. Trial Implant 100

Yet another alternative embodiment of a trial implant 100 is shown in FIGS. 3–3B. The trial implant 100 is highly similar to previous embodiments and includes a central body 102, a first tab 104 and a second tab 106. Once again, the central body 102 defines a superior face 108, an inferior face 110, an anterior side face 112, a posterior side face 114, a first end face 116 and a second end face 118. The first tab 104 and the second tab 106 extend from the first end face 116 and the second end face 118, respectively.

The composition and structure of the central body 102, the first tab 104 and the second tab 106 are virtually identical to those previously described with reference to the rectangular trial implant 20 (FIG. 1) and the tapered trial implant 60 (FIG. 2). The actual shape, however, of these components differs somewhat. In particular, the trial implant 100 assumes an angled, wedge-shaped, best shown in FIGS. 3A and 3B. For this reason, the trial implant 100 can be referred to as an "angled trial implant."

The angled trial implant 100 tapers in height (z-axis in FIG. 3B) from the posterior side face 114 to the anterior side face 112. Similar to the tapered trial implant 60 (FIG. 2), the first and second end faces 116, 118 each of the angled trial implant 100 are angled to form an included angle in the range of approximately 4–20 degrees, preferably 12 degrees. Additionally, the central body 102 tapers in length (y-axis in FIG. 3A) from the posterior side face 114 to the anterior side face 112 such that the superior and inferior faces 108, 110 are approximately trapezoidal. In particular, with reference to FIG. 3A, the central body 102 tapers in length (y-axis) between the anterior side face 112 and the posterior side face 114 to form an included angle in the range of approximately 40–60 degrees, preferably 50 degrees. It should be understood, however, that other angles, either greater or smaller, are also acceptable. Additionally, the superior face 108 and the inferior face 110 need not be identical.

The first and second tabs 104, 106 are preferably virtually identical, configured to be parallel to the first and second end faces 116, 118, respectively. For example, as best shown in FIG. 3A, the first tab 104 has a generally uniform length (y-axis) that is parallel to the orientation of the first end face 116. The second tab 106 has a similar relationship with respect to the second end face 118. Finally, the first and second tabs 104, 106 each include an opening 120.

As with previous embodiments, the angled trial implant 100 is preferably sized and shaped to generally correspond with the size and shape of an available prosthetic spinal disc nucleus. An example of one such angled prosthetic spinal disc nucleus 130 is shown in FIG. 3C. The angled prosthetic spinal disc nucleus 130 is generally comprised of a hydrogel core 132 and a constraining jacket 134. The constraining jacket 134 is secured about the hydrogel core 132 by closures 136 located at opposite ends of the hydrogel core 132. The hydrogel core 132 is pre-formed to assume an angled, tapered shape, and is configured to expand from a dehydrated state to a hydrated state. The constraining jacket 134 constrains expansion of the hydrogel core 132 in the hydrated state. The angled prosthetic spinal disc nucleus 130 is typically implanted in the dehydrated state, and can be fabricated to various dimensions while still maintaining the depicted angled shape.

Comparison of the trial implant 100 of FIG. 3 with the angled prosthetic spinal disc nucleus 30 of FIG. 3C illustrates the general correspondence of the size and shape of the angled trial implant 100 with the angled prosthetic spinal disc nucleus 130 (preferably in the dehydrated state). Because the angled trial implant 100 is representative of the angled prosthetic spinal disc nucleus 130 in terms of shape and size, the angled trial implant 100 can be used to evaluate whether the angled prosthetic spinal disc nucleus 130 is of an appropriate size for a particular disc space. In this regard, it should be noted that the first and second tabs 104, 106 correspond to the closures 136. It should be understood that the angled prosthetic spinal disc nucleus 130 shown in FIG. 3C is but one example of an available prosthesis. Other prosthetic nucleus devices are available that vary in size and construction from the one depicted in FIG. 3C. The angled trial implant 100 may be configured to correlate with the specific size and shape characteristics of these varying prostheses. As a result, depending on the particular design of the prosthesis, the first and/or second tabs 104, 106 may be eliminated from the angled trial implant 100.

In light of the above preference that the angled trial implant 100 conform to an available prosthesis, such as the angled prosthetic spinal disc nucleus 130 of FIG. 3C, certain dimensional attributes can be ascribed to one preferred embodiment of the angled trial implant 100. For example, the angled trial implant 100 tapers in length (y-axis in FIG. 3A) and has a maximum length (at the posterior side face 114 and including the first and second tabs 104, 106) in range of approximately 0.8–1.7 inches (≈20–43 mm), and a minimum length (at the anterior side face 112 and including the tabs 104, 106) in the range of approximately 0.4–1.2 inches (≈10–30.5 mm). As with previous embodiments, the central body 102 dictates the critical dimensions of the angled trial implant 100. The central body 102 tapers in height (z-axis in FIG. 3B), having a maximum height (at the posterior side face 114) in the range of approximately 0.10–0.50 inch (≈2.5–12.5 mm)and a minimum height (at the anterior side face 112) in the range of approximately 0.02–0.37 inch (≈0.5–9.5 mm). Further, the central body 102 has a width in the range of approximately 0.3–0.7 inch (≈7.5–17.5 mm). Finally, the central body 102 tapers in length (y-axis in FIG. 3A), having a maximum length (at the anterior side face 112) in the range of approximately 0.6–1.1 inches (≈15–28 mm) and a minimum length (at the posterior side face 114) in the range of approximately 0.2–0.6 inch (≈2.5–5 mm). The first and second tabs 104, 106 are virtually identical, each having a length (y-axis in FIG. 3A) in the range of approximately 0.1–0.3 inch (≈2.5–7.5 mm)and height in the range of approximately 0.1–0.2 inch. It should be recognized, however, that the above-provided dimensions can vary widely such that the angled trial implant 100 is sized to evaluate any individual disc space.

Because the angled trial implant 100 is sized to simulate an available prosthesis, such as the angled prosthetic spinal disc nucleus 130 shown in FIG. 3C, the angled trial implant 100 is preferably made available to a surgeon in a variety of sizes. For example, in one preferred embodiment, the central body 102 of the angled trial implant 100 can be provided in at least three different sizes, set forth in the following table:

assumes an angled, wedge-shape. With reference to FIGS. 4A and 4B, this configuration has a reverse angular shape when compared to the angled trial implant 100 (FIG. 3). For this reason, the alternative trial implant 140 can be referred to as a "reverse angled trial implant."

The reverse angled trial implant 140 again tapers in length (y-axis in FIG. 4A) from the posterior side face 154 to the anterior side face 152 such that the superior and inferior faces 148, 150 are approximately trapezoidal. In particular, with reference to FIG. 4A, the reverse angled trial implant 140 tapers in length between the posterior side face 154 and the anterior side face 152 to form an included angle in the range of approximately 40–60 degrees, preferably 50 degrees. It should be recognized, however, that other angles, either greater or smaller, are also acceptable. Additionally, the anterior and posterior side faces 152, 154 need not be identical or even symmetrical.

With reference to FIG. 4B, the reverse angle trial implant 140 also tapers in height (z-axis in FIG. 4B) from the anterior side face 152 to the posterior side face 154. In a preferred embodiment, the central body 142 tapers in height to form an included angle in the range of approximately 4–20 degrees, preferably 12 degrees. Other dimensions are acceptable, and the superior face 148 and the inferior face 150 need not be symmetrical.

In general terms, the reverse angle trial implant 140 is preferably sized and shaped to generally correspond with the size and shape of an available prosthetic spinal disc nucleus. An example of one such reverse angle prosthetic spinal disc nucleus 170 is shown in FIG. 4C. The reverse angle prosthetic spinal disc nucleus 170 is generally comprised of a

|   | Central Body 102 Maximum Height (z-axis) | Central Body 102 Minimum Height (z-axis) | Central Body 102 Maximum Length (y-axis) | Central Body 102 Minimum Length (y-axis) |
|---|---|---|---|---|
| 1 | 0.23 inch (5.8 mm) | 0.13 inch (3.3 mm) | 0.85 inch (21.6 mm) | 0.40 inch (10.2 mm) |
| 2 | 0.29 inch (7.4 mm) | 0.19 inch (4.8 mm) | 0.85 inch (21.6 mm) | 0.40 inch (10.2 mm) |
| 3 | 0.37 inch (9.4 mm) | 0.27 inch (6.9 mm) | 0.85 inch (21.6 mm) | 0.40 inch (10.2 mm) |

Regardless of the exact dimensions of the central body 102, the first tab and the second tab 104, 106 are preferably virtually identical, having a preferred length (y-axis) of 0.2 inch (≈5 mm) and a preferred height (z-axis) of 0.12 inch (≈3 mm).

D. Trial Implant 140

Yet another alternative embodiment of a trial implant 140 is shown in FIGS. 4B. The trial implant 140 is similar to previous embodiments and includes a central body 142, a first tab 144 and a second tab 146. Once again, the central body 142 defines a superior face 148, an inferior face 150, an anterior side face 152, a posterior side face 154, a first end face 156 and a second end face 158. The first tab 144 extends from the first end face 156, whereas the second tab 146 extends from the second end face 158. The first and second tabs 144, 146 are virtually identical, each including a hole 160.

The composition and structure of the central body 142, the first tab 144 and the second tab 146 are virtually identical to those previously described, with reference to the rectangular trial implant 20 of (FIG. 1), the tapered trial implant 60 (FIG. 2), and the angled trial implant 100 (FIG. 3). The actual shape, however, of the components differs somewhat. The trial implant 140, and in particular the central body 142, hydrogel core 172 and a constraining jacket 174. The constraining jacket 174 secured about the hydrogel core 172 by closures 176 located at opposite sides of the hydrogel core 172. The hydrogel core 172 is pre-formed to assume a reverse angled shape, and is configured to expand from a dehydrated state to a hydrated state. The constraining jacket 174 constrains expansion of the hydrogel core 172 in the hydrated state. The reverse angled prosthetic spinal disc nucleus 170 is typically implanted in the dehydrated state, and can be fabricated to various dimensions while still maintaining the depicted reverse angle shape.

Comparison of the reverse angle trial implant 140 of FIG. 4 with the reverse angle prosthetic spinal disc nucleus 170 of FIG. 4C illustrates the general correspondence in size and shape of the reverse angle trial implant 140 with the reverse angle prosthetic spinal disc nucleus 170 (preferably in the dehydrated state). Because of this relationship, the reverse angle trial implant 140 can be used to evaluate whether the reverse angle prosthetic spinal disc nucleus 170 is of an appropriate size for a particular disc space. In this regard, it should be noted that the first and second tabs 144, 146 are representative of the closures 176. It should be understood, however, that the reverse angle prosthetic spinal disc nucleus 170 shown in FIG. 4C is but one example of an available prosthesis. Other prosthetic nucleus devices are available that vary in size and construction from the one shown in FIG. 4C. Depending upon the particular prosthesis in question, the first and/or second tabs 144, 146 may be eliminated from the reverse angle trial implant 140.

Given the above preference that the reverse angle trial implant 140 correspond to a size and shape of the reverse angle prosthetic spinal disc nucleus 170, certain dimensions can be attributed to the reverse angle trial implant 140. For example, in one preferred embodiment, the reverse angle trial implant 140 tapers in length (y-axis in FIG. 4A) and has an overall maximum length at the posterior side face 154 and including the tabs 144, 146 in the range of approximately 0.92–1.6 inches (≈23.5–40.5 mm) and an overall minimum length (at the anterior side face 152 and including the tabs 144, 146) in the range of approximately 0.5–1.1 inches (≈12.5–28 mm). As with previous embodiments, the central body 142 dictates the critical dimensions of the reverse angle trial implant 170. The central body 142 tapers in length (y-axis in FIG. 4A), having a maximum length (at the posterior side face 154) in the range of approximately 0.6–1.0 inch (≈15–25.5) and a minimum length (at the anterior side face 152) in the range of approximately 0.2–0.6 inch (≈5–15 mm). Further, the central body 142 tapers in height (z-axis in FIG. 4B), having a maximum height (at the anterior side face 152) in the range of approximately 0.1–0.5 inch (≈2.5–12.5 mm) and a minimum height (at the posterior side face 154) in the range of approximately 0.05–0.25 inch (≈1–6.5 mm). Finally, the central body 142 has a width in the range of approximately 0.3–0.7 inch (≈7.5–18 mm). The first and second tabs 144, 146 have dimensions similar to those previously described with other embodiments of the present invention.

Because a surgeon is normally provided with different sized reverse angled prosthetic disc nuclei 170, the reverse angle trial implant 140 should also be provided in a variety of sizes. For example, one preferred embodiment of the present invention envisions at least three different reverse angle trial implants 140, having the central body 142 sized in accordance with the following table:

a frame sized to frictionally receive an appropriately sized one of the plurality of trial implants 184.

The container 182 is preferably a box having a cover (shown partially). The container 182 is preferably constructed from a rigid material able to withstand repeated sterilization. For example, the container 182 may be formed from stainless steel able to maintain its structural integrity when repeatedly processed through an autoclave. Further, the container 182 includes a plurality of passages 186 for facilitating sterilization of the plurality of trial implants 184 when the trial implant kit 180 is placed within a sterilization device, such as an autoclave.

The plurality of trial implants 184 preferably are the various trial implants previously described. For example, the plurality of trial implants 184 may include the rectangular trial implant 20 (FIG. 1), the tapered trial implant 60 (FIG. 2), the angled trial implant 100 (FIG. 3) and/or the reverse angle trial implant 140 (FIG. 4). As shown in FIG. 5, different sizes of each of the various trial implants (20, 60, 100, 140) are provided. It will be recalled that in preferred embodiments, the trial implant 20, 60, 100 or 140 is preferably manufactured to assume different sizes. Each one of these different sizes may be placed within the container 182. For example, three different sizes of the angled trial implant 100 are included in FIG. 5, having maximum widths of approximately 0.23 inch (5.8 mm), 0.29 inch (7.4 mm) and 0.37 inch (9.4 mm), respectively. An equal, greater or lesser number of other trial implants (e.g., the rectangular trial implant 20, the tapered trial implant 60 and/or the reverse angle trial implant 140) can also be provided. In other words, the trial implant kit 180 depicted in FIG. 5 is only one example of an acceptable kit. As will be made clear below, the trial implant kit 180 may contain as few as two, or more than one hundred, trial implants.

In conjunction with the differently sized and shaped trial implants comprising the plurality of trial implants 184, the container 182 preferably includes identification indicia 188. The identification indicia 188 is associated with each of the plurality of trial implants 184 and preferably provides a user

|   | Central Body 142 Maximum Height (z-axis) | Central Body 142 Minimum Height (z-axis) | Central Body 142 Maximum Length (y-axis) | Central Body 142 Minimum Length (y-axis) |
|---|---|---|---|---|
| 1 | 0.225 inch (5.7 mm) | 0.125 inch (3.2 mm) | 0.853 inch (21.7 mm) | 0.400 inch (10.2 mm) |
| 2 | 0.285 inch (7.2 mm) | 0.185 inch (4.7 mm) | 0.853 inch (21.7 mm) | 0.400 inch (10.2 mm) |
| 3 | 0.365 inch (9.3 mm) | 0.265 inch (6.7 mm) | 0.853 inch (21.7 mm) | 0.400 inch (10.2 mm) |

E. Trial Implant Kit 180

Trial implants in accordance with the present invention have been described as having a wide variety of sizes and shapes, with each shape being representative of an available prosthetic nucleus. As described in greater detail below, during use, a particular trial implant can be used to evaluate whether an associated prosthetic nucleus will "fit" within a particular disc space. To facilitate this procedure, a wide variety of trial implants are preferably provided to a surgeon in a singular kit. One example of a trial implant kit 180 is shown in FIG. 5. The trial implant kit 180 includes a container 182 and a plurality of trial implants 184. The plurality of trial implants 184 are selectively maintained within the container 182 for retrieval by a user (not shown). In this regard, the container 182 may include retaining means (not shown) for maintaining each of the plurality of trial implants 184. For example, the retaining means may be with an indication of the shape and size characteristics of a particular trial implant. The identification indicia 188 is preferably formed on the container 182 adjacent a respective one of the retaining means (not shown). For example, the identification indicia 188 may include a reference to a shape of a particular one of the plurality of trial implants 184 (such as rectangular, tapered, angled and/or reverse angle), a height of the particular one of the plurality of trial implants 184 and a length of that trial implant. Thus, the identification indicia 188 will be different for each one of the plurality of trial implants 184. It will be obvious to one of ordinary skill in the art that a wide variety of identification indicia 188 can be utilized to identify the shape and/or size of a particular trial implant.

One important feature of the trial implant kit 180 is that it can be repeatedly sterilized. For example, following the use of one or more of the plurality of trial implants 184 to evaluate a disc space (described in greater detail below), all of the plurality of trial implants 184 are placed at an appropriate location within the container 182. The entire trial implant kit 180 is then processed through a sterilization device (not shown), such as an autoclave. The autoclave effectuates sterilization of the trial implant kit 180 by subjecting the trial implant kit 180 to pressurized steam. The autoclave is normally fitted with a gauge that automatically regulates an internal pressure, and therefore the degree of heat to which the trial implant kit 180 is subjected. Notably, the container 182 includes the plurality of passages 186 to allow the pressurized steam to interact with the plurality of trial implants 184. Following sterilization, trial implant kit 180 is removed from the sterilization device and is available for subsequent use. Thus, the trial implant kit 180, including the plurality of trial implants 184, can be repeatedly used to evaluate multiple disc spaces because the trial implant kit 180 can be resterilized after each use.

F. Method of Use

One preferred method of using the trial implant 20, 60, 100 or 140 of the present invention is shown in FIGS. 6–10. As shown in FIGS. 6–10, the trial implant 20, 60, 100 or 140 is used to evaluate a damaged disc space 200. For example, the trial implant 20, 60, 100 or 140 may be used to determine whether a similarly sized prosthetic spinal disc nucleus will "fit" within the disc space 200. The disc space 200 separates two adjacent vertebrae 202 and includes an anulus 204 and a nucleus region 206 (shown best in FIGS. 8 and 9). Posterior access to the anulus 204 is achieved by performing a laminotomy in a targeted lamina area 208. The laminotomy is normally performed adjacent an opening 210 formed in the anulus 204. The opening 210 may be a naturally occurring tear in the anulus 204 (for example, where the disc space 200 has herniated). Alternatively, the opening 210 may be created in the anulus 204 following the laminotomy, such as by removing a plug of material from the anulus 204. Even further, the opening 204 may be generated by creating a retractable flap in the anulus 204. Regardless of the exact configuration, the opening 210 provides access to the nucleus region 206. Excess nucleus material is removed from the nucleus region or cavity 206 to provide room for implantation of a prosthesis.

The surgeon then selects an appropriately sized trial implant for placement within the nucleus cavity 206. For example, the surgeon may be provided with the trial implant kit 180 (FIG. 5) containing the plurality of trial implants 184 (FIG. 5). The particular trial implant selected by the surgeon will depend upon a general estimate of the size of the nucleus cavity 206 based upon the patient's (not shown) height, weight and spinal extension. Further, the surgeon's trial implant selection will vary depending upon the particular location of the disc space 200 (for example, between the L4 and L5 vertebrae, between the L5 and S1 vertebrae, etc.) and whether the prosthetic spinal disc nucleus corresponding to the particular trial implant will be positioned at an anterior area 212 or posterior area 214 of the nucleus cavity 206. As an additional selection aide, a depth caliper may be employed to estimate the transverse diameter of the nucleus cavity 206 at the anterior area 212 or the posterior area 214. Even further, a contrast material may be injected into the nucleus cavity 206 and viewed via a fluoroscope. With this criteria in mind, any one of the previously described trial implants, including the rectangular trial implant 20 (FIG. 1), the tapered trial implant 60 (FIG. 2), the angled trial implant 100 (FIG. 3) or the reverse angle trial implant 140 (FIG. 4) are available. Further, it should be understood that for each one of the trial implants 20, 60, 100 or 140 described, a variety of different sizes may be available. For example, the surgeon may first determine that the disc space 200 requires implantation of the tapered prosthetic spinal disc nucleus 90 of FIG. 2C at the anterior area 212 of the nucleus cavity 206. Based upon the patient's size and weight (and potentially in conjunction with measurements taken with a depth caliper), the surgeon will select the largest tapered trial implant 60 he or she believes will fit at the anterior area 212.

Figure 8:
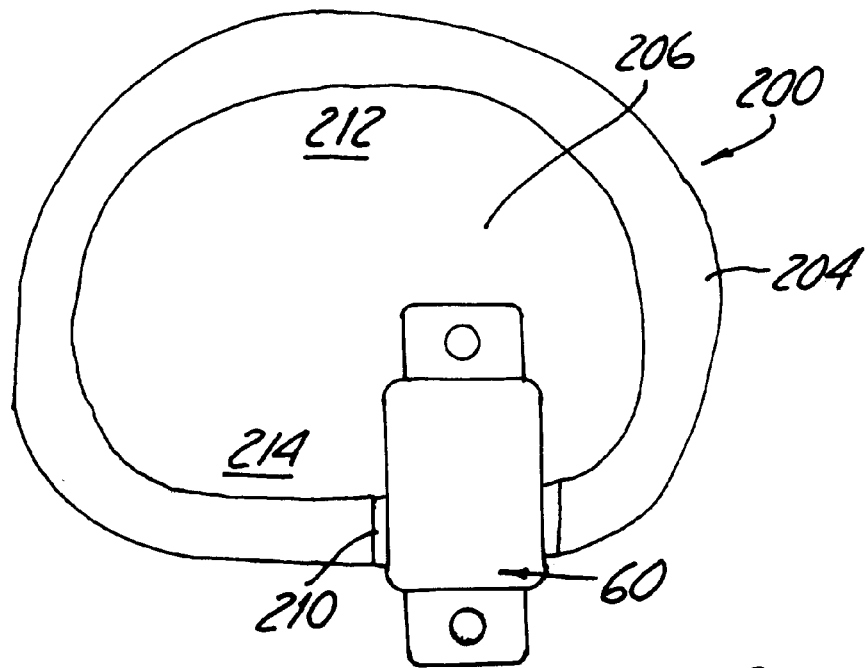
FIGS. 8–10 illustrate insertion of a properly sized trial implant into a nucleus cavity.

Once a trial implant has been selected, the surgeon then attempts to insert that trial implant into the nucleus cavity 206. FIG. 8 depicts partial insertion of the tapered trial implant 60 into the nucleus cavity 206. As shown in FIG. 8, the tapered trial implant 60 is directed through the opening 210 in the anulus 204. Where the opening 210 in the anulus 204 is properly sized, the anterior side face 72 and the posterior side face 74 will not contact (or will "clear") the anulus 204 tissue defining the lateral walls of the opening 204. Typically, the superior face 68 and the inferior face 70 (FIG. 2) will be in contact with the anulus 204 tissue and are therefore relatively smooth to facilitate movement along the anulus 204.

Figure 7:
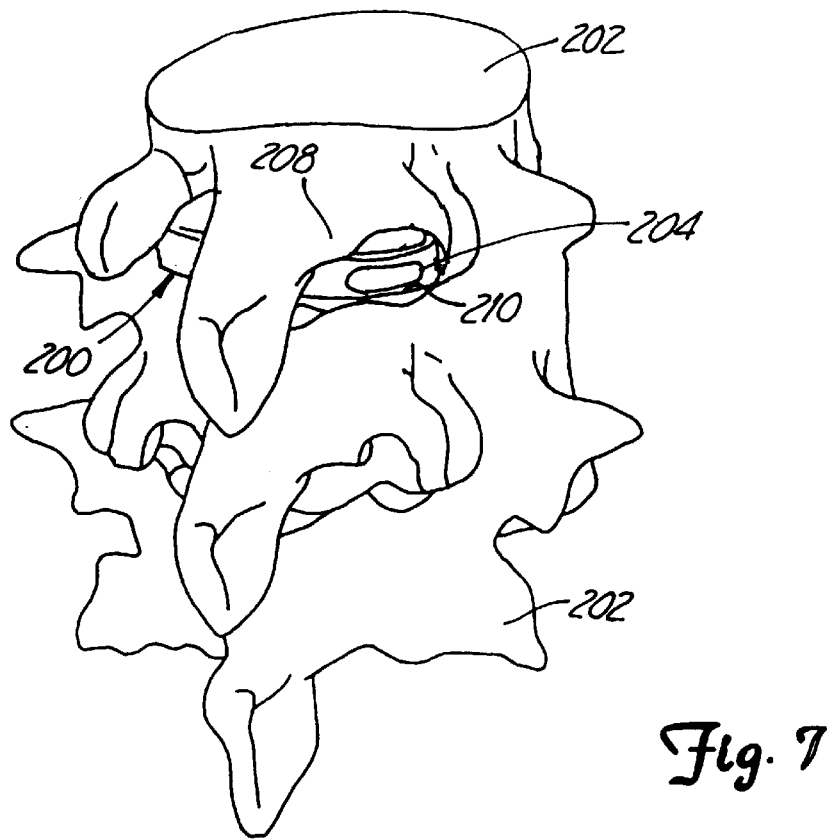
FIG. 7 is a posterior view of a portion of a human spine, showing an opening through an anulus.

The surgeon continues to move the tapered trial implant 60 distally into the nucleus cavity 206 until the entire tapered trial implant 60 is within the nucleus cavity 206. The surgeon then attempts to rotate the tapered trial implant 60 ninety degrees to the position shown in FIG. 9. Once rotated, the surgeon attempts to forcibly position the tapered trial implant to a desired area of the nucleus cavity 206, such as the anterior area 212. This may include the use of a separate force applying tool. As previously described, by utilizing a tough material, the trial implant 20, 60, 100 or 140 will not alter in shape in response to this auxiliary force. The relatively smooth nature of the superior face 68 and the inferior face 70 (FIG. 2) promotes movement of the tapered trial implant 60 between the adjacent vertebrae 202 (FIG. 7).

Figure 9:
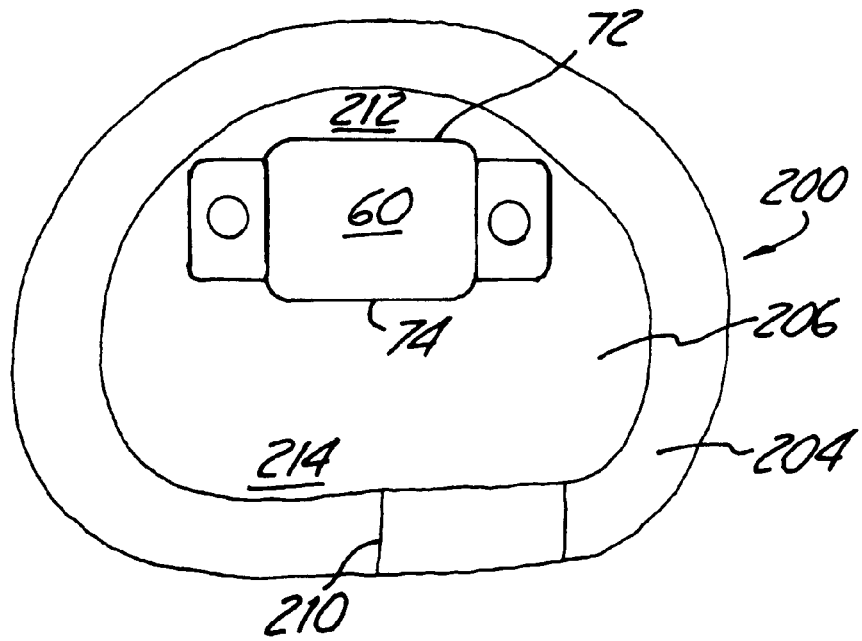
Figure 10:
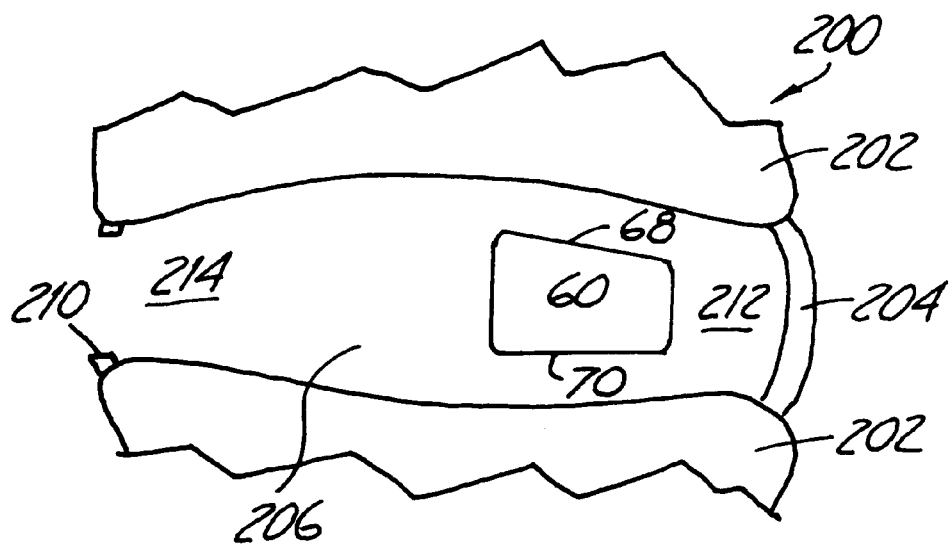

As depicted in FIG. 9, the tapered trial implant 60 extends transversely across the disc space 200, adjacent the anterior area 212 of the nucleus cavity 206. The anterior side face 72 is adjacent a portion of the anulus 204, whereas the posterior side face 74 is centrally located within the nucleus cavity 206. This positioning is likewise depicted in FIG. 10. Once again, the tapered trial implant 60 has been positioned adjacent the anterior area 212 of the nucleuscavity 206. The superior face 68 is adjacent an upper one of the opposing vertebrae 202, whereas the inferior face 70 is adjacent a lower one of the opposing vertebrae 202. If the surgeon is able to position the tapered trial implant 60 as shown in FIGS. 9 and 10, the surgeon can confidently conclude that a similarly sized prosthetic spinal disc nucleus (such as the tapered prosthetic spinal disc nucleus 90 shown in FIG. 2C) will "fit" within the anterior area 212 nucleus cavity 206 upon subsequent implantation. If desired, the surgeon may attempt to place a second trial implant (not shown) in the posterior area 214 of the nucleus cavity 206. Notably, the above-described procedure for inserting the tapered trial implant 60 applies equally to other trial implant embodiments, such as the rectangular trial implant 20 (FIG. 1), the angled trial implant 100 (FIG. 3) and the reverse angle trial implant 140 (FIG. 4).

Figure 11:
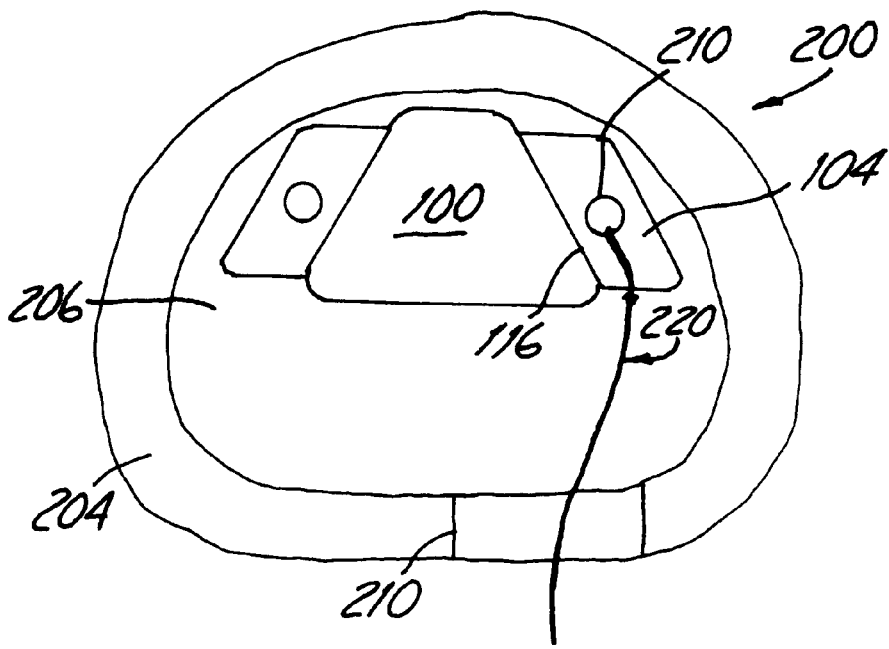

After the surgeon evaluates the disc space 200 as described above, the trial implant is then removed from the nucleus cavity 206. In this regard, the trial implant is preferably provided with a retrieving means for facilitating removal from the disc space 200. One example of a retrieval means 220 associated with the angled trial implant 100 is shown in FIG. 11. The retrieving means 220 depicted in FIG. 11 is a suture secured to the first tab 104 of the angled trial implant 100. Alternatively, a flexible thread or similar material may be used. During the above-described implantation procedure, a portion of the suture 220 remains exterior the anulus 204, passing through the opening 210. The angled trial implant 100 is removed from the disc space 200 by simply pulling on the suture 220. In response, the suture 220 guides the angled trial implant 100 toward the opening 210, such that the angled trial implant 100 extends in a generally sagitall direction within the nucleus cavity 206, generally aligned with the opening 210. At a certain point during retraction of the suture 220, the first tab 104 and the first end face 116 of the angled trial implant 100 will be exposed through the opening 210 in the anulus 206. From this position, the surgeon is able to grasp the first tab 104 and remove the angled trial implant 100 from the disc space 200.

An alternative approach for retrieving the trial implant is depicted in FIG. 12. More particularly, FIG. 12 shows the rectangular trial implant 20 and a retrieval tool 230. The retrieval tool 230 includes a handle 232 and a shank 234. The shank 234 includes a proximal portion 236 and a distal portion 238. The distal portion 238 extends from the proximal portion 236 to form a 90 degree angle, and terminates in a shoulder 240. The distal portion 238 of the tool 230 is sized to be selectively secured to the first tab 24 of the rectangular trial implant 20. More particularly, the distal portion 238 of the tool 230 is sized to pass through the opening 40 in the first tab 24. Thus, in the embodiment shown in FIG. 12, the first tab 24, including the opening 40, constitutes a retrieving means. During use, the rectangular trial implant 20 (or any other trial implant embodiment) is retrieved by directing the shank 234 of the tool 230 toward the rectangular trial implant 20. The distal portion 238 of the tool 230 is then directed through the opening 40 of the first tab 24. Once the distal portion 238 has passed through the opening 40, the shoulder 240 prevents the distal portion 238 from readily disengaging from the first tab 24. Once secured, the retrieval tool 230 is retracted from the disc space 200 (FIG. 9). The rectangular trial implant 20, via connection to the tool 230 at the first tab 24, is likewise retracted from the disc space 200.

Yet another alternative embodiment of a retrieving means is shown in FIG. 13. FIG. 13 depicts a trial implant 250 (which may be a rectangular trial implant, tapered trial implant, angled trial implant, reverse angle trial implant or other embodiment) having a central body 252 and opposing tabs 254. One of the opposing tabs 254 of the trial implant 250 is shown as presenting a grasping surface for grasping by a hemostat 256. Hemostats are well known in the art and generally comprise an elongated tool having a scissors-like distal end by which a surgeon may apply a compressive or pinching force. With the embodiment shown in FIG. 13, the opposing tabs 254 constitute retrieving means. During use, the surgeon (not shown) simply directs the hemostat 256 to grasp one of the opposing tabs 254 along the grasping surface. Once secured to the hemostat 256, the hemostat 256 and the trial implant 250 can be removed from the disc space 200 (FIG. 9). It should be recognized that a hemostat can also be used to assist in inserting the trial implant 250 as well. Importantly, because the trial implant 250 material is preferably tough, the tab 254 will not break away from the central body 250 when a shearing force is applied to the tab 254 by the hemostat 256. With the approach of FIG. 13, it should be understood that the opposing tabs 254 need not include the previously-described opening. Additionally, only one of the opposing tabs 254 is required to facilitate retrieval of the trial implant 250.

Figure 14:
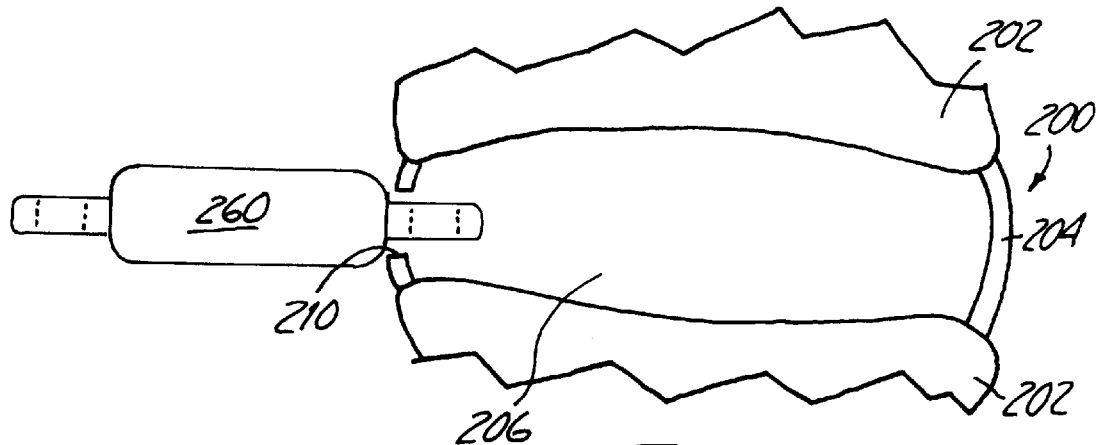
FIG. 14 is a lateral, sectional view of a disc space and an improperly sized trial implant.

As described above, the trial implant of the present invention is used to evaluate various spacing considerations associated with a disc space. In this regard, FIGS. 8–10, along with the associated description, presented use of a trial implant that was properly sized for a particular disc space. One benefit of the present invention, however, is that a surgeon can also determine whether a particular trial implant is too large or too small for a particular disc space. For example, FIG. 14 depicts attempted insertion of a trial implant 260 into the disc space 200. The trial implant 260 may be the rectangular trial implant 20 (FIG. 1), the tapered trial implant 60 (FIG. 2), the angled trial implant 100 (FIG. 3), the reverse angle trial implant (FIG. 4), or other similar designs. The disc space 200 includes the opposing vertebrae 202, the anulus 204 and the nucleus cavity 206. The anulus 204 includes the opening 210. As shown in FIG. 14, the trial implant 260 is too large to pass through the opening 210 in the anulus 204. In other words, as the surgeon (not shown) attempts to insert the trial implant 260 through the opening 210, the anulus 204 impedes insertion into the nucleus cavity 206. During this attempt, however, the surgeon will likely notice a spring-like resistance to insertion of the trial implant 260. In this regard, the trial implant 260 does not contact the adjacent vertebrae 202, which would otherwise provide a more definitive resistance or "hard stop" to movement of the trial implant 260. Based upon this perception, the surgeon will determine that the opening 210 in the anulus 204 is too small to allow passage of the trial implant 260, and therefore should attempt to enlarge the opening 210. After the opening 210 has been enlarged, a second attempt will be made to insert the trial implant 260.

Figure 15:
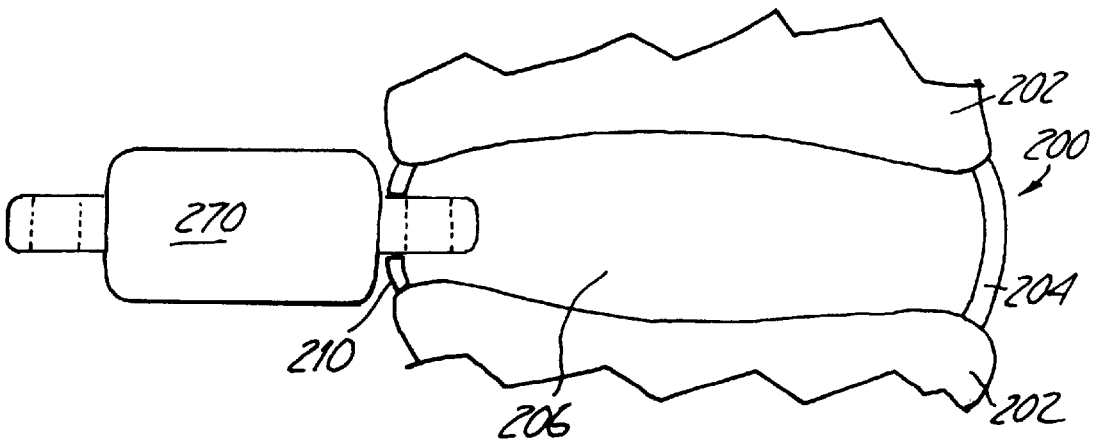
FIG. 15 is a lateral, sectional view of a disc space and an improperly sized trial implant.

Another possible relationship between a trial implant 270 and the disc space 200 is shown in FIG. 15. Once again, the trial implant 270 may be any one of the trial implants 20, 60, 100 or 140 previously described, or other design. The trial implant 270 is too large relative to the disc space 200. As the surgeon (not shown) attempts to insert the trial implant 270 through the opening 210 in the anulus 204, a portion of the trial implant 270 contacts the opposing vertebrae 202. Due to the rigid nature of the opposing vertebrae 202, the surgeon will sense a hard stop to movement of the trial implant 270. Under these circumstances, the surgeon will conclude that the trial implant 270 is too large for the disc space 200, and will subsequently attempt to insert a differently sized trial implant.

Figure 16:
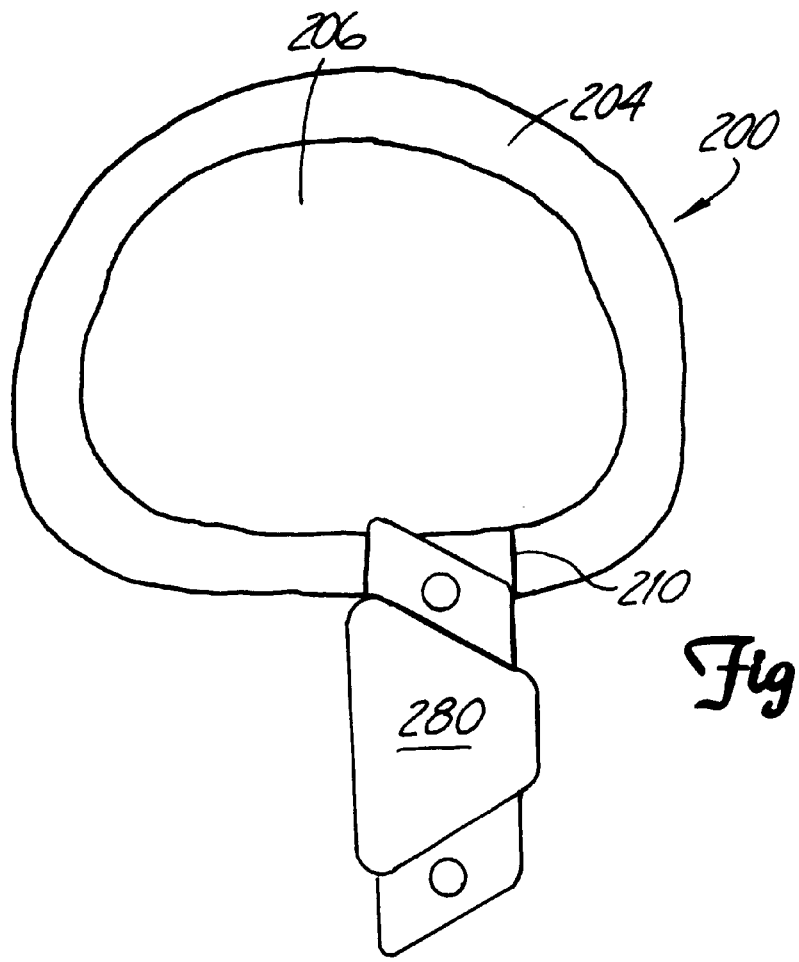
FIG. 16 is a top, sectional view of a disc space and an improperly sized trial implant.

In addition to having a height greater than a height of the opening 210 (as shown in the example of FIG. 14), the trial implant may also be too wide for the opening 210. This problem is represented in FIG. 16, which includes a trial implant 280 and the disc space 200. Once again, the trial implant 280 may be any one of the trial implants 20, 60, 100 or 140 previously described. As shown in FIG. 16, the trial implant 280 is wider than the opening 210 in the anulus 204. Under these circumstances, assuming the trial implant does not contact the opposing vertebrae 202 (FIG. 15), the surgeon will sense a spring-like resistance as the trial implant 280 contacts the anulus 204. Based on a visual evaluation of the disc space 200, the surgeon will determine that the opening 210 is too small and requires enlargement. Once the opening 210 has been enlarged, a second attempt will be made to insert the trial implant 280.

Figure 17:
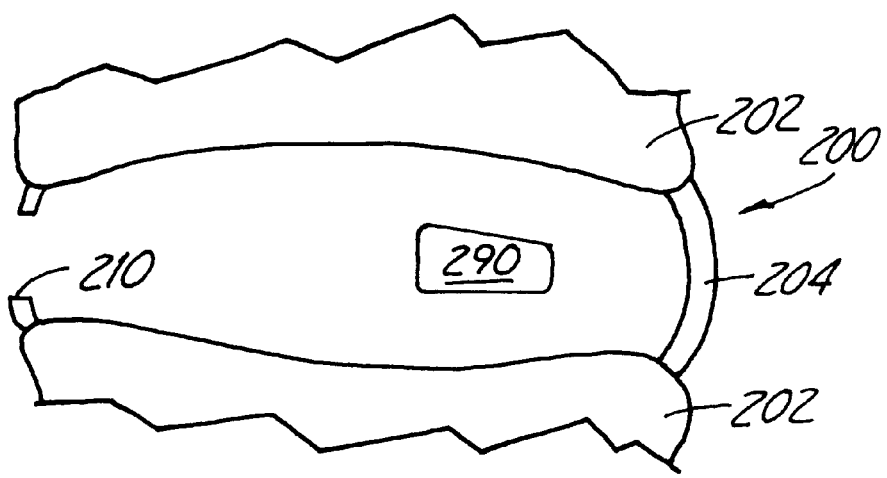
FIG. 17 is a lateral, sectional view of a disc space and an improperly sized trial implant.

Finally, it is possible that a particular trial implant may be too small for a particular disc space. An example of this scenario is shown in FIG. 17 which includes a trial implant 290 (which may be any one of the previously described trial implants 20, 60, 100 or 140) implanted within the disc space 200. Where the trial implant 290 is too small for the particular disc space 200, the trial implant 290 will easily slide to the anterior area 212 of the nucleus cavity 206. In other words, the trial implant 290 does not "tightly" fit between the adjacent vertebrae 202. When the surgeon senses that the trial implant 290 is too small, the trial implant 290 is removed from the disc space 200. Subsequently, an attempt is made to implant a larger trial implant and again evaluate its relationship to a size of the disc space 200.

The trial implant of the present invention provides an inexpensive, reusable device for evaluating a disc space. Because the trial implant closely resembles, in terms of shape and size, an available prosthetic spinal disc nucleus, a surgeon is able to quickly ascertain whether that prosthetic spinal disc nucleus will "fit" within a disc space. In this regard, once the trial implant has been used to evaluate the disc space, the trial implant can be sterilized and reused. Finally, by providing a kit containing a number of differently sized trial implants, a surgeon can determine with relative confidence the size of a prosthetic spinal disc nucleus required by a particular disc space.

Although the present invention has been described with reference to preferred embodiments, workers skilled in the art will recognize that changes may be made in form and detail without departing from the spirit and scope of the invention. For example, while the trial implant has been described with reference to rectangular, tapered, angled, and reverse angled shapes, other designs are equally acceptable. So long as the trial implant resembles an available prosthetic spinal disc nucleus, that trial implant can be used to evaluate whether or not the particular prosthetic spinal disc nucleus will fit within the disc space. Similarly, the various trial implant embodiments have each included two opposing tabs. These tabs have been provided to resemble a stitching feature associated with one available form of a prosthetic spinal disc nucleus. Thus, with reference to a prosthetic spinal disc nucleus that does not include any lateral extensions, one or both of the opposing tabs can be eliminated. Additionally, the various faces of the trial implants have all been described as preferably being relatively smooth. To facilitate insertion of the trial implant, however, it is only necessary that the superior and inferior face be relatively smooth. Even further, in some instances, all faces may be relatively rough yet the trial implant will still perform the desired evaluation function.

What is claimed:

1. A trial implant for evaluating a size of a nucleus cavity portion of an intradiscal space, the nucleus cavity defined by an opposing pair of vertebral bodies and an anulus, the trial implant comprising:

an elongated central body defining a superior face, an inferior face, opposing side faces and opposing end faces, the central body being formed of a rigid, surgically safe material and having a volume less than a volume of a nucleus cavity; and a tab associated with the elongated central body for facilitating retrieval of the elongated central body from a nucleus cavity;

wherein a combination of the central body and the tab is sized to be encompassed by the anulus.

2. The trial implant of claim 1, wherein the superior face and the inferior face are relatively smooth.

3. The trial implant of claim 2, wherein the opposing side faces and the opposing end faces are relatively smooth.

4. The trial implant of claim 1, wherein the elongated central body is substantially rectangular.

5. The trial implant of claim 1, wherein the elongated central body is substantially wedge-shaped.

6. The trial implant of claim 5, wherein the superior face and the inferior face extend in an angular fashion from a first one of the opposing side faces to a second one of the opposing side faces such that the first opposing side face has a height less than a height of the second opposing side face.

7. The trial implant of claim 6, wherein each of the opposing end faces is approximately trapezoidal.

8. The trial implant of claim 5, wherein the opposing end faces extend in an angular fashion from a first one of the opposing side faces to a second one of the opposing side faces such that the first opposing side face has a length less than a length of the second opposing side face.

9. The trial implant of claim 8, wherein the top face and the bottom face are approximately trapezoidal.

10. The trial implant of claim 1, where the elongated central body is made of an autoclave-sterilizable material.

11. The trial implant of claim 1, wherein the elongated central body has a height in the range of approximately 0.1 to 0.5 inch.

12. The trial implant of claim 1, wherein the elongated central body has a width in the range of approximately 0.2 to 0.5 inch.

13. The trial implant of claim 1, wherein the elongated central body has a maximum length in the range of approximately 0.3 to 1.7 inches.

14. The trial implant of claim 1, wherein the tab extends extending from one of the opposing end faces.

15. The trial implant of claim 14, further including:

a second tab extending from one of the opposing end faces opposite the first tab.

16. The trial implant of claim 14, wherein the tab forms a hole.

17. The trial implant of claim 16, wherein the retrieving means further includes a thread secured to the tab.

18. A trial implant for evaluating a size of a nucleus cavity portion of an intradiscal space, the nucleus cavity defined by an opposing pair of vertebral bodies and an anulus, the trial implant comprising:

an elongated body having a volume less than a volume of a nucleus cavity and being formed from a rigid, non-porous material; and a tab associated with the elongated body for facilitating retrieval of the elongated body from a nucleus cavity.

wherein a combination of the elongated body and tab is sized to be encompassed by the anulus.

19. The trial implant of claim 18, wherein the elongated body has a size and shape corresponding with a size and shape of an available prosthetic spinal disc nucleus.

20. The trial implant of claim 18, wherein the elongated body is made of an inert material.

21. The trial implant of claim 18, wherein the elongated body is made of a low-friction material.

22. The trial implant of claim 18, wherein the elongated body is made of a tough material.

23. The trial implant of claim 18, wherein the elongated body is polyvinylideneflouride.

24. The trial implant of claim 18, wherein the trial implant is made of an autoclave-sterilizable material.

25. A kit for use in evaluating a size of a nucleus cavity for receiving a prosthetic spinal disc nucleus, the nucleus cavity defined by an opposing pair of vertebral bodies and an anulus, the kit comprising:

a container;

a first trial implant maintained within the container, the first trial implant being formed of a rigid, surgically safe material and having a predetermined size and shape related to a size and shape of a nucleus cavity; and a second trial implant maintained within the container, the second trial implant being formed of a rigid, surgically safe material and having a predetermined size and shape, wherein the size of the first trial implant is different than the size of the second trial implant.

26. The kit of claim 25, wherein the shape of the second trial implant is different than the shape of the first trial implant.

27. The kit of claim 25, wherein the shape and size of the first trial implant corresponds with a shape and size of an available first prosthetic spinal disc nucleus.

28. The kit of claim 27, wherein the shape and size of the second trial implant corresponds with a shape and size of an available second prosthetic spinal disc nucleus.

29. The kit of claim 25, wherein the container includes first indicia associated with the first trial implant, the first indicia indicative of a characteristic of the first trial implant.

30. The kit of claim 25, wherein the container further includes second indicia associated with the second trial implant, the second indicia identifying a characteristic of the second trial implant.

31. The kit of claim 25, wherein the first trial implant and the second trial implant are made of an autoclave-sterilizable material.

32. The kit of claim 25, wherein the container is made of an autoclave-sterilizable material.

33. A method of evaluating a size of an intradiscal space for receiving a prosthetic spinal disc nucleus, the space including an intradiscal nucleus cavity defined by an opposing pair of vertebral bodies and an anulus, the method comprising:

creating an opening in the anulus to provide access to the nucleus cavity;

inserting a trial implant into the nucleus cavity through the opening, the trial implant being of a rigid, surgically safe material and having a predetermined size and shape;

attempting to position the trial implant within a desired area of the nucleus cavity;

determining whether the trial implant fits within the desired area of the nucleus cavity; and removing the trial implant from the nucleus cavity.

34. The method of claim 33, wherein the size and shape of the trial implant correspond with a size and shape of an available prosthetic spinal disc nucleus.

35. The method of claim 33, wherein the desired area of the nucleus cavity is adjacent an anterior side of the anulus.

36. The method of claim 33, wherein the shape and size of the available prosthetic spinal disc nucleus dictates a desired orientation of the prosthetic spinal disc nucleus within the nucleus cavity upon implantation, and wherein attempting to position the trial implant includes:

maneuvering the trial implant to a position corresponding with the desired orientation.

37. The method of claim 33, wherein determining whether the trial implant fits within the desired portion includes:

evaluating whether the trial implant body is larger than the desired area of the nucleus cavity.

38. The method of claim 33, further including:

selecting the trial implant from a plurality of trial implants based upon an estimate of the size of the desired area, wherein each of the plurality of trial implants has a different size.

39. The method of claim 33, further including:

sterilizing the trial implant after removal from the nucleus cavity.

40. The method of claim 39, further including:

reusing the trial implant to evaluate a second nucleus cavity.

\* \* \* \* \*